(12) United States Patent
Song et al.

(10) Patent No.: US 7,894,891 B2
(45) Date of Patent: Feb. 22, 2011

(54) DIFFUSION-BASED MAGNETIC RESONANCE METHODS FOR CHARACTERIZING BONE STRUCTURE

(75) Inventors: Yi-Qiao Song, Ridgefield, CT (US);
Eric E. Sigmund, New York, NY (US);
HyungJoon Cho, Somerville, MA (US)

(73) Assignee: Schlumberger Technology Corporation, Ridgefield, CT (US)

( * ) Notice: Subject to any disclaimer, the term of this patent is extended or adjusted under 35 U.S.C. 154(b) by 1156 days.

(21) Appl. No.: 11/478,033

(22) Filed: Jun. 29, 2006

(65) Prior Publication Data

US 2007/0238969 A1   Oct. 11, 2007

Related U.S. Application Data

(60) Provisional application No. 60/761,517, filed on Jan. 24, 2006.

(51) Int. Cl.
*A61B 5/04* (2006.01)
(52) U.S. Cl. ...................................... 600/546
(58) Field of Classification Search ............... 600/546
See application file for complete search history.

(56) References Cited

U.S. PATENT DOCUMENTS 6,249,692 B1 * 6/2001 Cowin .................. 600/407

| 6,285,901 B1 | 9/2001 | Taicher et al. |
| 6,850,060 B2 * | 2/2005 | Song et al. .................. 324/303 |
| 2003/0057947 A1 | 3/2003 | Ni et al. |

FOREIGN PATENT DOCUMENTS

EP    1367406 B1    2/2007

OTHER PUBLICATIONS

Valfouskaya et al, Nuclear Magnetic Resonance Diffusion Simulations in Porous Media, Journal of Applied Physics, 97,083510 p. 1-10, 2005.*
Song, Using internal magnetic fields to obtain pore size distributions of porous media, Concepts in Magnetic Resonance Part A: Magnetic Resonance Engineering, vol. 18A Issue 2, pp. 97-110, Jun. 2003.*
Song, Pore sizes and pore connectivity in rocks using the effect of internal field, Magnetic Resonance Imaging, vol. 19, Issue 3, p. 417-421, Apr. 2001.*
Fyhrie, Direct calculation of the surface-to-volume ratio for human cancellous bone, Journal of Biomechanics 26(8): 955-967, 1993.*

(Continued)

*Primary Examiner*—Long V Le
*Assistant Examiner*—Saurel J Selkin
(74) *Attorney, Agent, or Firm*—James McAleenan; Vincent Loccisano; Brigid Laffey

(57) ABSTRACT

A method of in vitro or in vivo nuclear magnetic resonance and/or magnetic resonance imaging, to determine bone properties by measuring the effects of molecular diffusion inside the bone specimen to derive parameters that are related to the structure of the trabecular bones. The method is a non-invasive probe that provides topological information on trabecular bone without requiring a full high-resolution image of its structure, and is compatible with clinical use.

28 Claims, 16 Drawing Sheets

OTHER PUBLICATIONS

Basser, P. J., et al., Estimation of the Effective Self-Diffusion Tensor from the NMR Spin Echo, Journal of Magnetic Resonance, Series B, 1994, pp. 247-254, vol. 103, Issue 3.

Boehm, H. F., et al., Prediction of the Biomechanical Strength of Bone by Analysis of Local 3D-Scaling Properties Extracted From High Resolution MRI of Human Trabecular Bone in Comparison With Bone Mineral Density In Vitro, Bone, 2003, p. S78, vol. 32, Issue 5.

Borgia, G. C. et al., Scaling of Spin-Echo Amplitudes with Frequency, Diffusion Coefficient, Pore Size, and Susceptibility Difference for the NMR of Fluids in Porous Media and Biological Tissues, Physical Review E, 1995, pp. 2104-2114, vol. 51, No. 3.

Borgia, G. C., et al., The Effect of Diffusion and Susceptibility Differences on T2 Measurements for Fluids in Porous Media and Biological Tissues, Magnetic Resonance Imaging, 1996, pp. 731-736, vol. 14, Issues 7-8.

Borgia, G. C., et al., Uniform-Penalty Inversion of Multiexponential Decay Data, Journal of Magnetic Resonance, 1998, pp. 65-77, vol. 132, Issue 1.

Callaghan, P. T., et al., Diffusion in Porous Systems and the Influence of Pore Morphology in Pulsed Gradient Spin-Echo Nuclear Magnetic Resonance Studies, Journal of Chemical Physics, 1992, pp. 651-662, vol. 97, Issue 1.

Callaghan, P. T., Principles of Nuclear Magnetic Microscopy, 1993, pp. 371-419, Oxford University Press, NY, NY.

Chen, Q., et al., A Magnetic Resonance Study of Pore Filling Processes During Spontaneous Inhibition in Berea Sandstone, Journal of Chemical Physics, 2003, pp. 9609-9616, vol. 119, No. 18.

Chung, H., et al., Relationship Between NMR Transverse Relaxation, Trabecular Bone Architecture, and Strength, Proceedings of the National Academy of Sciences, USA, 1993, pp. 10250-10254, vol. 90.

Cory, D. G., et al., Measurement of Translational Displacement Probabilities by NMR: An Indicator of Compartmentation, Magnetic Resonance in Medicine, 1990, pp. 435-444, vol. 14.

Cowin, S. C., The Relationship Between the Elasticity Tensor and the Fabric Tensor, Mechanics of Materials, 1985, pp. 137-147, vol. 4, Issue 2.

Engelke, K., et al., Phantom Studies Simulating the Impact of Trabecular Structure on Marrow Relaxation Time, T2', Magnetic Resonance in Medicine, 1994, pp. 380-387, vol. 31, No. 4.

Fordham, E. J., et al., Imaging Multiexponential Relaxation in the (y, log e T1) Plane, with Application to Clay Filtration in Rock Cores, 1995, Journal of Magnetic Resonance, Series A, 1995, pp. 139-150, vol. 113, Issue 2.

Genant, H. K., et al., (editors), Bone Densitometry and Osteoporosis, 1998, pp. 1-19, 269-290, 305-334, Springer, Berlin, Germany.

Goldstein, S. A., et al., Measurement and Significance of Three-Dimensional Architecture to the Mechanical Integrity of Trabecular Bone, Calcified Tissue International, 1993 pp. S127-S133, vol. 53, Suppl. 1.

Helmer, K. G. et al., The Application of Porous Media-Theory to the Investigation of Time-Dependent Diffusion in In Vivo Systems, NMR in Biomedicine, 1995, pp. 297-306, vol. 8, Issue 7.

Hurlimann, M. D., et al., Restricted Diffusion in Sedimentary Rocks. Determination of Surface-Area-to-Volume Ratio and Surface Relaxivity, Journal of Magnetic Resonance, Series A, 1994, pp. 169-178, vol. 111, Issue 2.

Hurlimann, M. D. Effective Gradients in Porous Media Due to Susceptibility Differences, Journal of Magnetic Resonance, 1998, pp. 232-240, vol. 131, Issue 2.

Hwang, S. N., et al., The Calculation of the Susceptibility-Induced Magnetic Field from 3D NMR Images with Applications to Trabecular Bone, Journal of Magnetic Resonance, Series B, 1995, pp. 126-145, vol. 109, Issue 2.

Hwang, S. N., et al., Experimental Evaluation of a Surface Charge Method for Computing the Induced Magnetic Field in Trabecular Bone, Journal of Magnetic Resonance, 1999, pp. 35-45, vol. 139, Issue 1.

Hwang, S. N., et al., Subvoxel Processing: A Method for Reducing Partial Volume Blurring With Application to In Vivo MR Images of Trabecular Bone, Magnetic Resonance in Medicine, 2002, pp. 948-957, vol. 47, Issue 5.

Kroeker, R. M., et al., Analysis of Biological NMR Relaxation Data with Continuous Distributions of Relaxation Times, Journal of Magnetic Resonance, 1986, pp. 218-235, vol. 69, Issue 2.

Laib, A. et al., New Model-Independent Measures of Trabecular Bone Structure Applied to In Vivo High-Resolution MR Images, Osteoporosis International, 2002, pp. 130-136, vol. 13, No. 2.

Latour, L. L., et al., Time-Dependent Diffusion Coefficient of Fluids in Porous Media as a Probe of Surface-to-Volume Ratio, Journal of Magnetic Resonance, Series A, 1993, pp. 342-346, vol. 101, Issue 3.

Link, T. M., et al., Structure Analysis of High Resolution Magnetic Resonance Imaging of the Proximal Femur: In Vitro Correlation with Biomechanical Strength and BMD, Calcified Tissue International, 2003, pp. 156-165, vol. 72, No. 2.

Link, T. M., et al., High-Resolution MRI vs Multislice Spiral CT: Which Technique Depicts the Trabecular Bone Structure Best?, European Radiology, 2003, pp. 663-671, vol. 13, No. 4.

Ma, J., et al., Method for Image-Based Measurement of the Reversible and Irreversible Contribution to the Transverse-Relaxation Rate, Journal of Magnetic Resonance, Series B, 1996, pp. 61-69, vol. 111, Issue 1.

Majumdar, S., et al., Studies of Diffusion in Random Fields Produced by Variations in Susceptibility, Journal of Magnetic Resonance, 1988, pp. 41-55, vol. 78, Issue 1.

Majumdar, S., et al., Correlation of Trabecular Bone Structure with Age, Bone Mineral Density, and Osteoporotic Status: In Vivo Studies in the Distal Radius Using High Resolution Magnetic Resonance Imaging, Journal of Bone and Mineral Research, 1997, pp. 111-118, vol. 12, No. 1.

Majumdar, S., et al., High-Resolution Magnetic Resonance Imaging: Three Dimensional Trabecular Bone Architecture and Biomechanical Properties, Bone, 1998, 445-454, vol. 22, No. 5.

Mitra, P. P., et al., Short-Time Behavior of the Diffusion Coefficient as a Geometrical Probe of Porous Media, Physical Review B, 1993, pp. 8565-8574, vol. 47, No. 14.

Newitt, D. C., et al., Decay Characteristics of Bone Marrow in the Presence of a Trabecular Bone Network: In Vitro and In Vivo Studies Showing a Departure form Monoexponential Behavior, Magnetic Resonance in Medicine, 1996, pp. 921-927, vol. 35, No. 6.

Ouyang, X., et al., High Resolution Magnetic Resonance Imaging of the Calcaneus: Age-Related Changes in Trabecular Structure and Comparison with Dual X-Ray Absorptiometry Measurements, Calcified Tissue International, 1997, pp. 139-147. vol. 60, No. 2.

Parfitt, A. M., Implications of Architecture for the Pathogenesis and Prevention of Vertebral Fracture, Bone, 1992, S41-S47, vol. 13, Suppl. 2.

Sen, P. N., et al., Surface Relaxation and the Long-Time Coefficient in Porous Media: Periodic Geometries, Physical Review B, 1994, pp. 215-230, vol. 49, No. 1.

Sen, P. N., Time-Dependent Diffusion Coefficient as a Probe of Geometry, Concepts in Magnetic Resonance, Part A, 2004, pp. 1-21, vol. 23A, Issue 1.

Song, Y. Q., Detection of the High Eigenmodes of Spin Diffusion in Porous Media, Physical Review Letters, 2000, pp. 3878-3881, vol. 85, No. 18.

Song, Y. Q., Determining Pore Sizes Using an Internal Magnetic field, Journal of Magnetic resonance, 2000. pp. 397-401, vol. 143, Issue 2.

Song, Y. Q., et al., Determining Multiple Length Scales in Rocks, Nature, 2000, pp. 178-181, vol. 406.

Song, Y. Q., et al., Pore Geometry and its Geological Evolution in Carbonate Rocks, Petrophysics, 2002, pp. 420-424, vol. 43, No. 5.

Song, Y. Q., Using Internal Magnetic Fields to Obtain Pore Size Distributions of Porous Media, Concepts in Magnetic Resonance, Part A, 2003, pp. 97-110, vol. 18A, Issue 2.

Song, Y. Q., et al., Determining the Resolution of Laplace Inversion Spectrum, The Journal of Chemical Physics, 2005, pp. 104104-1-104104-8, vol. 122.

Staph, S., et al., (editors), NMR Imaging in Chemical Engineering, 2006, pp. 340-358, Wiley-VCH, 2006, Germany.

Stejskal, E. O., et al., Spin Diffusion Measurements: Spin Echoes in the Presence of a Time-Dependent Field Gradient, The Journal of Chemical Physics, 1965, pp. 288-292, vol. 42, No. 1.

Tanner, J. E., Use of the Stimulated Echo in NMR Diffusion Studies, The Journal of Chemical Physics, 1970, pp. 2523-2526, vol. 52, No. 5.

Tikhonov, A. N., et al., Solutions of Ill Posed Problems, 1997, pp. 45-108, John Wiley & Sons, Washington, D.C.

Torrey, H. C., Bloch Equations with Diffusion Terms, Physical Review, 1956, pp. 563-565, vol. 104, No. 3.

Woessner, D. E., N.M.R. Spin-Echo Self-Diffusion Measurements on Fluids Undergoing Restricted Diffusion, The Journal of Physical Chemistry, 1963, pp. 1365-1367, vol. 67, No. 6.

Wu, E. X., et al., Effect of Diffusion on the Steady-State Magnetization with Pulsed Field Gradients, Journal of Magnetic Resonance, 1990, pp. 243-253, vol. 90, Issue 2.

Audoly, B., et al., Correlation functions for inhomogeneous magnetic field in random media with application to a dense random pack of spheres, Journal of Magnetic Resonance, 2003, pp. 154-159, vol. 164.

Basser, P.J., , Inferring Microstructural Features and the Physiological State of Tissues From Diffusion-Weighted Images, NMR in Biomedicine, 1995, pp. 333-344, vol. 8.

Bouchard, L.-S., et al., Structural anisotropy and internal magnetic fields in trabecular bone: Coupling solution and solid dipolar interactions, Journal of Magnetic Resonance, 2005, pp. 27-36, vol. 176.

Capuani, S., et al., Characterization of Trabecular Bone by Dipolar Demagnetizing Field MRI, Magnetic Resonance in Medicine, 2001, pp. 683-689, vol. 46.

Chin, C.-L., et al., Isolating quantum coherences in structural imaging using intermolecular double-quantum coherence MRI, Journal of Magnetic Resonance, 2003, pp. 309-314, vol. 165.

Chung, H.-W., et al., Quantitative Analysis of Trabecular Microstructure by 400 MHz Nuclear Magnetic Resonance Imaging, Journal of Bone and Mineral Research, 1995, pp. 803-811. vol. 6, No. 5.

Chung, H.-W., et al., Three-Dimensional Nuclear Magnetic Resonance Microimaging of Trabecular Bone, Journal of Bone and Mineral Research, 1995, pp. 1452-1461, vol. 10, No. 10.

Gomberg, B.R., et al., Topology-based orientation analysis of trabecular bone networks, Medical Physics, Feb. 2003, pp. 1-11. vol. 30, No. 2.

Greenspan, S.L., et al., Femoral Bone Loss Progresses With Age: A Longitudinal Study in Women Over Age 65, Journal of Bone and Mineral Research, 1994, pp. 1959-1965, vol. 9, No. 12.

Hahn, E.L., Spin Echos, Physical Review, Nov. 1950, pp. 580-601, vol. 80, No. 4.

Han, S., et al., Ultrasound Velocity and Boradband Attenuation Over a Wide Range of Bone Mineral Denisty, Osteoporosis International, 1996, pp. 291-296, vol. 6.

Jara, F.W., et al., High-Resolution Variable Flip Angle 3D MR Imaging of Trabecular Microstructure in Vivo, Magnetic Resonance in Medicine, 1993, pp. 528-539, vol. 29.

Karlicek, R. F., et al., A Modified Pulsed Gradient Technique for Measuring Diffusion in the Presence of Large Background Gradients*, Journal of Magnetic Resonance, 1980, pp. 75-91, vol. 37.

Kiselev, V.G., Calculation of diffusion effect for arbitrary pulse sequences, Journal of Magnetic Resonance, 2003, pp. 205-211, Vo. 164.

Kleerekoper, M., et al., The Role of Three-Dimensional Trabecular Microstructure in the Pathogenesis of Vertebral Compression Fractures, Calcified Tissue International, 1985, pp. 594-597, vol. 37.

Link, T.M., et al., In Vivo High Resolution MRI of the Calcaneus: Differences in Trabecular Structure in Osteoporosis Patients, Journal of Bone and Mineral Research, 1998, pp. 1175-1182, vol. 13, No. 7.

Lisitza, N.V., et al., The behavior of diffusion eigenmodes in the presence of internal magnetic field in porous media, Journal of Chemical Physics, 2001, pp. 9120-9124, vol. 114, No. 20.

Lisitza, N.V., et al., Study of diffusion in erythrocyte suspension using internal magnetic field inhomogeneity, Journal of Magnetic Resonance, 2007, pp. 146-154, vol. 187.

Mitra, P. P., et al., Diffusion Propagator as a Probe of the Structure of Porous Media, Physical Review Letters, 1992, vol. 68, No. 24.

Moore, J.R., et al., Solid State Phosphorus-31 Magnetic Resonance Imaging of Bone Mineral, Magnetic Resonance in Medicine, 1995, pp. 293-299, vol. 33.

Newitt, D.C., et al., In Vivo Assessment of Architecture and Micro-Finite Element Analysis Derived Indices of Mechanical Properties of Trabecular Bone in the Radius, Osteoporosis International, 2002, pp. 6-17, vol. 13.

Parfitt, A.M., Age-Related Structural Changes in Trabecular and Cortical Bone: Cellular Mechanisms and Biomechanical Consequences, Calcified Tissue International, 1984, pp. s123-s128, vol. 36.

Pothuaud, L., et al., Three-Dimensional-Line Skeleton Graph Analysis of High-Resolution Magnetic Resonance Images: A Validation Study From 34-µM-Resolution Microcomputed Tomography, Journal of Bone and Mineral Research, 2002, pp. 1883-1895, vol. 17, No. 10.

Robson, M.D., et al., Human Imaging of Phosphorus in Cortical and Trabecular Bone in Vivo, Magnetic Resonance in Medicine, 2004, pp. 888-892, vol. 51.

Rossi, C., et al., DTI of trabecular bone marrow, Magnetic Resonance Imaging, 2005, pp. 245-248, vol. 23.

Saha, P.K., et al. Predicting Mechanical Competence of Trabecular Bone Using 3D Tensor-Scale Based Parameters, Proc. of SPIE, 2005, pp. 279-290, vol. 5746.

Van Lenthe, G. H., et al., The Prospects of Estimating Trabecular Bone Tissue Properties from the Combination of Ultrasound, Dual-Energy X-Ray Absorptiometry, Microcomputed Tomography, and Microfinite Element Analysis*, Journal of Bone and Mineral Research, 2001, pp. 550-555, vol. 16, No. 3.

Wald, M., et al., Study of Trabecular Bone Microstructure using Spatial Autocorrelation Analysis, Proc. of SPIE, 2005, pp. 291-302, vol. 5746.

Wehrli, F. W., et al., Cancellous Bone Volume and Structure in the Forearm: Noninvasive Assessment with MR Microimaging and Image Processing, Radiology, 1998, pp. 347-357, vol. 206, No. 2.

Weinstein, R. S., et al., Decreased Trabecular Width and Increased Trabecular Spacing Contribute to Bone Loss with Aging, Bone, 1987, pp. 137-142, vol. 8.

Williams, W. D., et al. A Pulsed-Gradient Multiple-Spin-Echo NMR Technique for Measuring Diffusion in the Presence of Background Magnetic Field Gradients*, Journal of Magnetic Resonance, 1978, pp. 271-282, vol. 31.

Wolff, J., Maquet P., Furlong R. trans., The Law of Bone Remodelling, Berlin Germany: Springer-Verlag, 1986, pp. 85-87, 89-120.

Canny, J. A Computational approach to edge detection, Transactions on Pattern Analysis and Machine Intelligence, vol. PAMI-8, No. 6, Nov. 1986, pp. 679-698.

Kim et al., Effects of thresholding techniques on µCT-based finite element models on Trabecular Bone, Journal of Biomechanical Engineering, vol. 129, Aug. 2007, pp. 481-486.

Capuani, S., et al., Diffusion tensor imaging to study anisotrophy in a particular porous system: The trabecular bone network, Solid State Nuclear Magnetic Resonance, vol. 28, 2005, pp. 266-272.

Song, Y., et al., Determining multiple length scales in rocks, Nature, vol. 406, Jul. 13, 2000, pp. 178-181; Song, Y., et al., Errata, determining multiple length scales in rocks, Nature, vol. 407, Oct. 5, 2000, p. 654.

Yeung, D., et al., Bone Marrow Diffusion in Osteoporosis: Evaluation with Quantitative MR Diffusion Imaging, Journal of Magnetic Resonance Imaging, vol. 19, 2004, pp. 222-228.

Wehrli, F.W., et al. Noninvasive Assessment of Bone Architecture by Magnetic Resonance Micro-Imaging-Based Virtual Bone Biopsy, Proceedings of the IEEE, vol. 91, No. 10, Oct. 2003, pp. 1520-1542.

Fantazzini, P., et al., Bone tissue and porous media: common features and differences studied by NMR relaxation, Magnetic Resonance Imaging, vol. 21, 2003, pp. 227-234.

* cited by examiner

FIG. 2A
FIG. 2B
FIG. 2C
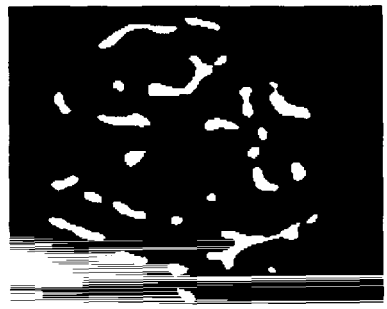
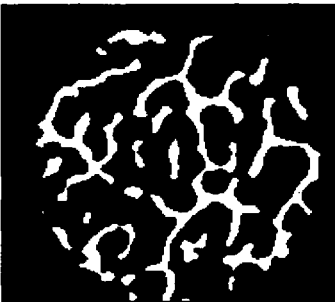
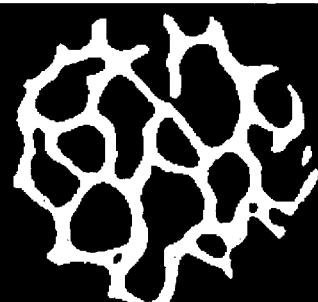
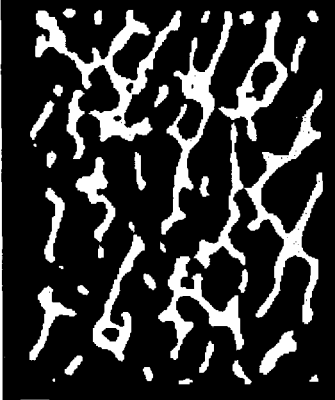
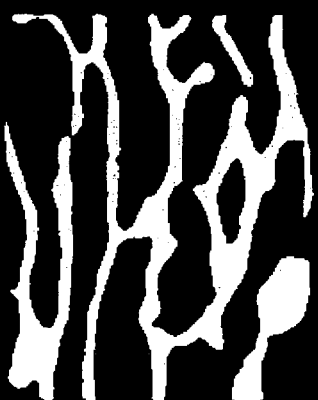
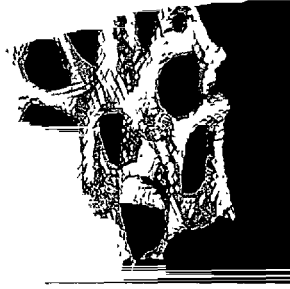
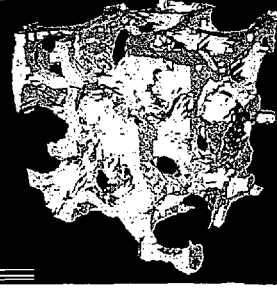
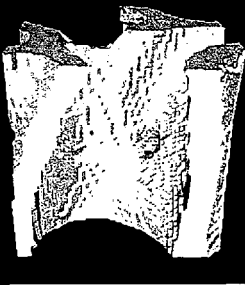

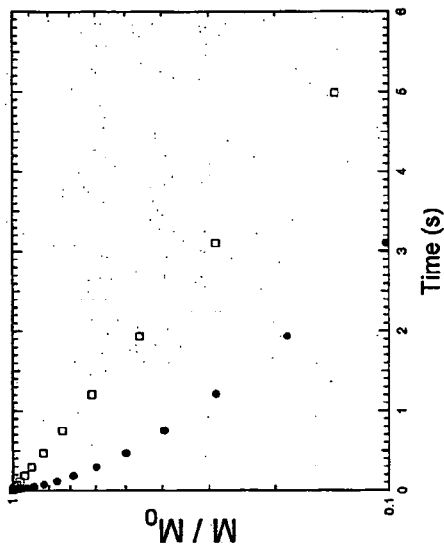
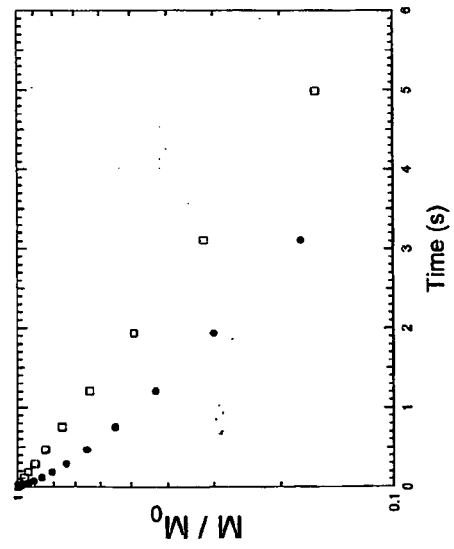
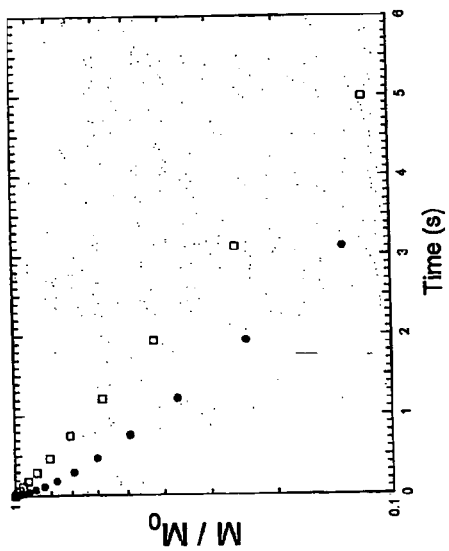

FIGURE 9A
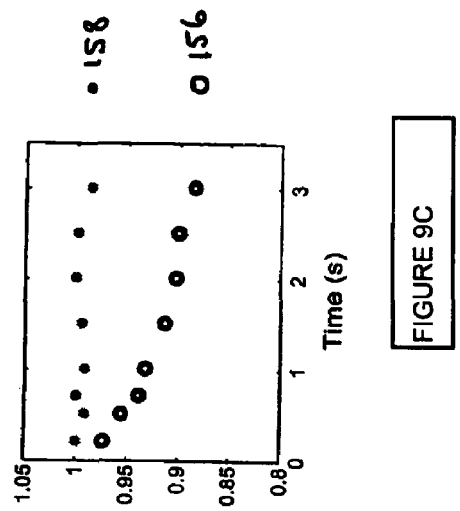
FIGURE 9B
FIGURE 9C

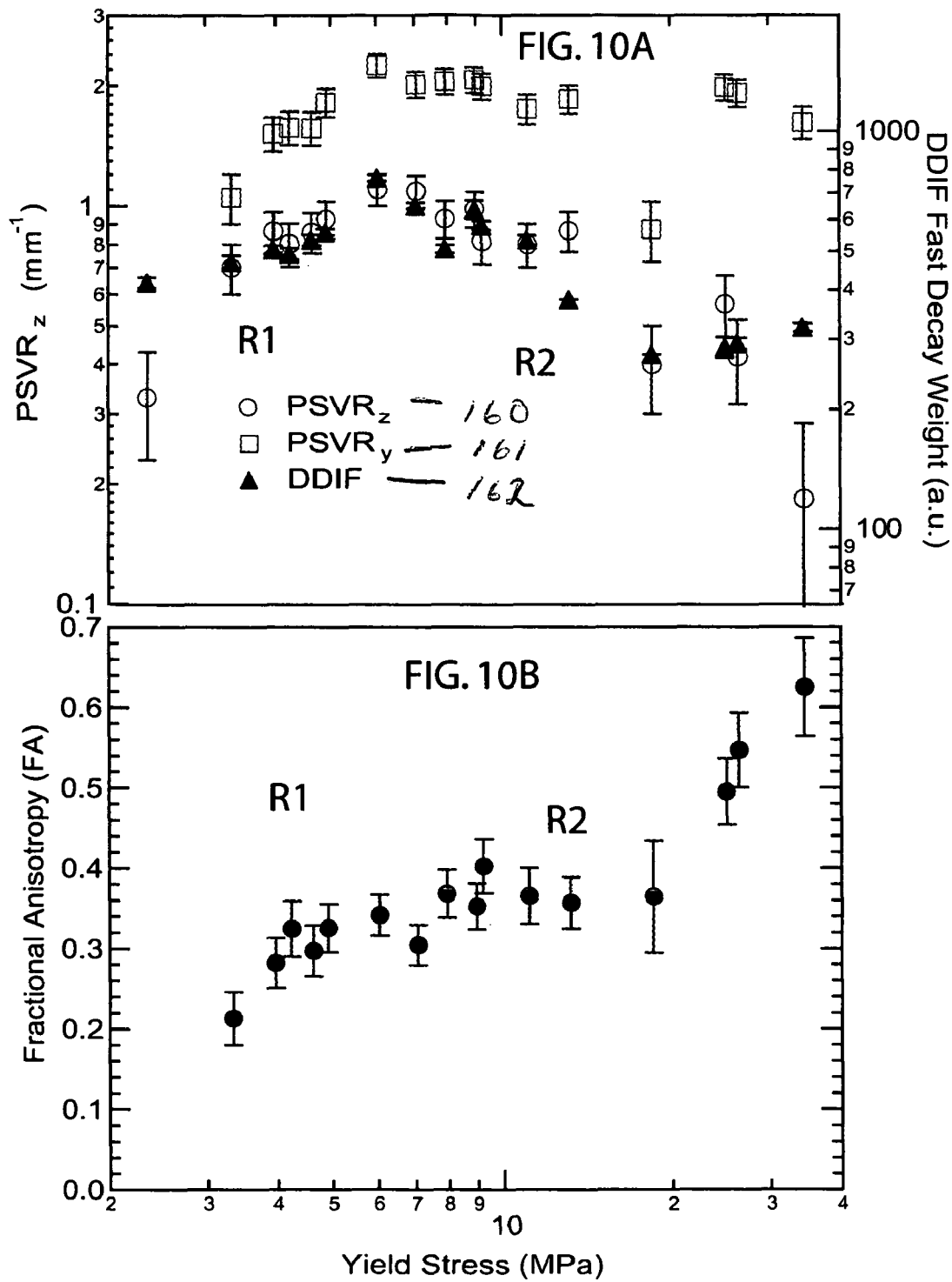

DIFFUSION-BASED MAGNETIC RESONANCE METHODS FOR CHARACTERIZING BONE STRUCTURE

CROSS-REFERENCE TO RELATED APPLICATIONS

The present application claims the benefit under 35 U.S.C. §119(e) of the earlier filing date of U.S. Provisional Application No. 60/761,517, entitled "DIFFUSION-BASED MAGNETIC RESONANCE METHODS FOR BONE STRUCTURE AND EVOLUTION" and filed on Jan. 24, 2006, which is herein incorporated by reference in its entirety.

GOVERNMENT INTERESTS

The present invention was developed at least in part with funds from NIH Grant No. 1R21 EB003869-01. The United States Government may have certain rights in the invention.

BACKGROUND

1. Field of Invention

The present invention is directed to improved methods for characterizing materials such as trabecular bone.

2. Discussion of Related Art

A major component of the human musculoskeletal system is bone, which supports our body weight, facilitates motion, and plays critical roles in mineral homeostasis and production of blood cells. Osteoporosis is a disorder of the skeleton in which bone strength is abnormally weak and susceptible to fractures from minor trauma. Regions of the human body for which the risk is greatest include the spine, hips and legs. In the United States, about 30 million people have osteoporosis and almost 19 million more have low bone density. Approximately 700,000 vertebral fractures, 250,000 hip fractures and 200,000 distal radius fractures occur annually in the United States, and billions of dollars are expended each year for the care of osteoporosis in the U.S. Therapeutic treatments of osteoporosis are under intense development.

Clinical assessment of osteoporosis presently relies mainly upon bone mineral density (BMD) measurements. Two common techniques clinically used to determine BMD are dual X-ray absorptiometry (DXA) and ultrasound. DXA measures the absorption of X-rays by the bone tissue, mostly by calcite minerals. In DXA, X-ray irradiation at two different energies is employed to distinguish the X-ray absorption of bone from that of soft tissue. The amount of absorption provides a measure of bone density. DXA is currently the gold standard in osteoporosis screening. Ultrasound measures speed and attenuation of sound waves in bone to predict BMD. However, the error associated with this technique can be significantly larger than that associated with DXA.

A drawback of BMD measurements is that the measured BMD is a gross average quantity and gives no information about either the structural integrity or the mechanical properties of the bone. While there is some correlation of bone mineral density with mechanical strength (the property determining fracture risk), there is a significant variation around the average correlation. For example, in FIG. 1, there is illustrated a graph of a relationship between bone strength and BMD for a set of excised human trabecular bone specimens. Apparent modulus (in MPa), a measure of the bone strength, is represented on the vertical axis, and apparent density (BMD) is represented on the horizontal axis. Line 102 illustrates a correlation between the two quantities. As can be seen in FIG. 1, there is an extensive spread of bone strength at a given density. While a definite correlation between BMD and fracture occurrence exists, it is also clear that densitometry alone does not entirely predict the risk of fracture. This is because the details of the trabecular bone structure (e.g., the "bone quality") and its evolution over time also contribute significantly to the strength of the bone and thus to the risk of fracture.

It is generally believed that bone microstructure, also referred to as bone quality, may have a significant impact on bone strength. Several medical imaging techniques, such as nuclear magnetic resonance (NMR), magnetic resonance imaging (MRI) and microscopic computed tomography (μCT) have been used to extract structural information about bone samples. μCT is one example of a microscopic imaging technique. Through a series of X-ray radiographs acquired at different orientations, a three-dimensional image of the bone matrix may be constructed. This technique may be used to create an image with voxel resolution as fine as a few μm. A "voxel" is three-dimensional measure of resolution, analogous to the two-dimensional "pixel." Compared to DXA, μCT is more sensitive to detecting bone loss, but at the expense of requiring a much higher X-ray dosage and is not currently viable for clinical use.

NMR and high-resolution MRI studies of bone in vitro and in vivo have been conducted in the research community. Bone is a highly (~80%) porous medium consisting of a calcified solid matrix with soft marrow, fat, microvasculature and water filling the pore space. The MRI image of bone is actually the signal of the marrow space because the solid bone tissue does not produce much MRI signal under standard clinical conditions. Three-dimensional images of bone with resolutions of 56 μm have been obtained from small samples. Results of such MRI imaging have included a wide range of topological properties that correlate with bone strength of the sample. In vivo imaging is presently at a resolution above 100 μm and sophisticated subvoxel processing has been tested to further enhance the resolution. From this direct measurement of bone structure, topological parameters can be derived which theoretically and empirically relate to bone strength. However, high resolution MRI is currently limited to the wrist and has not been applied to hip or spine.

Another property from which MR methods derive structural sensitivity is the difference in magnetic susceptibility between the solid and intervening tissue/fluids. When the static magnetic field required for the NMR measurement is applied, this susceptibility contrast gives rise to spatial variations of the magnetic field within the pore space. For example, the broadening ($1/T_2'$) of the resonance line due to the magnetic susceptibility contrast between the bone matrix and the intervening marrow can be measured. This broadening depends on the bone architecture, which in turn may provide a correlation of bone strength. The contribution of the static field inhomogeneity ($1/T_2'$) to the total NMR linewidth ($1/T_2^*$) has been measured in vitro and in vivo for a variety of bone samples and subjects, and has been found to correlate with strength parameters such as Young's modulus of elasticity. However, ($1/T_2'$)-based measurements have not yet reached the point of routine clinical use.

SUMMARY OF THE INVENTION

A primary clinical need of bone characterization in humans is the diagnosis of such disorders as osteoporosis, in which abnormally weak bone strength leads to high fracture susceptibility. The standard techniques of dual X-ray absorptiometry (DXA) and ultrasound determine bone mineral density (BMD) and have been used clinically to assess the fracture risk. However, density alone does not account for the full bone strength variation because the internal bone structure, apart from the bone density, contributes significantly to the mechanical strength of the bone. As a result, methods that rely on bone density measurements do not entirely predict fracture risk, and their clinical value is therefore limited. Although high resolution magnetic resonance imaging techniques may provide three-dimensional imaging of the trabecular architecture, which may be useful for osteoporosis diagnosis, their clinical application may be difficult. Specifically, it is difficult to improve the resolution of such imaging techniques far beyond their current levels (about 100 µm) in clinical implementation, primarily due to clinically allowed X-ray radiation dosage and the MRI scan time. Therefore, these methods also may have limited clinical use.

Accordingly, there is a need for a method of fracture risk assessment that is reliable and compatible with clinical use. Aspects and embodiments of the invention are directed to a different approach to the characterization of bone architecture than the high-resolution imaging approach. According to one embodiment, there is provided a method for trabecular bone strength determination using nuclear magnetic resonance (NMR) and magnetic resonance imaging (MRI) techniques. Various embodiments of methods according to aspects of the invention differ from conventional MRI methods because methods according to embodiments of the invention measure water diffusion as a way to characterize bone structure, and because they may not require high-resolution imaging.

According to one embodiment, an NMR technique that is well-established in inorganic porous media may be used to obtain statistical properties of the trabecular structure. This technique, referred to as decay from diffusion in an internal field, or DDIF, can obtain pore structure characteristics at a resolution of about 1 µm. As discussed below, DDIF data on bovine bone samples shows a clear correlation with bone strength. Furthermore, the DDIF data demonstrates a strong correlation with the projected surface-to-volume ratio and exhibits two regimes at the high and low bone strength. These two regimes may be interpreted as two types of bone-weakening behaviors, one by the loss of bone density at the low strength and the other by the change of bone architecture at the high strength. Correlation between the DDIF results and structural properties of bone samples observed in microscopic images suggest that the DDIF data may be used to characterize bone structure. Therefore, in some embodiments, DDIF measurements may provide a reliable indication of bone strength and may thus be used to assess bones, without the need for high resolution imaging.

According to an alternate embodiment, there is provided a method of in vitro or in vivo nuclear magnetic resonance and/or magnetic resonance imaging, to determine bone properties by measuring the effects of molecular diffusion inside the bone specimen to derive parameters that are related to the structure of the trabecular bones. The method is a non-invasive probe that provides some topological information on trabecular bone without requiring a full high-resolution image of its structure. The topological information can also be correlated via trends exemplified herein with mechanical properties such as yield stress. This correlation may provide an assay of bone strength relevant to diagnosis of osteoporosis. In some examples, methods of the invention may be applied to determine structural parameters and properties of bone, for example, surface to volume ratio, orientationally weighted S/V, pore sizes, Young's modulus, and the yielding stress. In other examples, there may be provided a procedure to extract and analyze the aforementioned topological information as an average surface-to-volume ratio. This information may be gleaned from a DDIF experiment as recited previously. Furthermore, in other embodiments, analogous procedures using pulsed-field-gradients rather than internal field gradients may be employed, yielding similar or complementary information.

According to one embodiment, a method of strength estimation for a trabecular bone sample may comprise measuring an effect of molecular diffusion inside the trabecular bone sample using a magnetic resonance technique to provide measured data, deriving a parameter from the measured data that is related to a structure of the trabecular bone sample, and estimating the strength of the trabecular bone sample from the parameter. In one example, the method may further comprise estimating the strength of the trabecular bone sample based on the parameter and the bone volume fraction. In another example, the method may further comprise calculating a bone mineral density of the trabecular bone sample, and estimating the strength of the trabecular bone sample may include estimating the strength of the trabecular bone sample based on the parameter and the bone mineral density. In another example, the parameter derived may be a surface-to-volume ratio of the trabecular bone sample.

Another embodiment of the invention is directed to a procedure for obtaining an indication of a bone structure including measuring diffusion within a sample of the bone, repeating the diffusion measurements at multiple times, obtaining statistical information based on the diffusion measurements, and extracting at least one bone property from the statistical information so as to provide the indication of bone structure. In one example, at least one bone property includes a surface to volume ratio of the bone. In another example, measuring diffusion may include measuring magnetization decay as a result of diffusion in an internal magnetic field of the bone.

BRIEF DESCRIPTION OF THE DRAWINGS

Various embodiments and aspects of the invention are described in detail below with reference to the accompanying figures. It is to be appreciated that the accompanying drawings, are not intended to be drawn to scale. In the drawings, each identical or nearly identical component that is illustrated in various figures is represented by a like numeral. For purposes of clarity, not every component may be labeled in every drawing. In the drawings:

FIG. 2A contains computed tomography images of sections of a bone sample;

FIG. 2B contains computed tomography images of sections of another bone sample;

FIG. 2C contains computed tomography images of sections of yet another bone sample;

FIG. 5A is a graph of normalized signal decay rate as a function of time for the bone sample of FIG. 2A;

FIG. 5B is a graph of normalized signal decay rate as a function of time for the bone sample of FIG. 2B;

FIG. 5C is a graph of normalized signal decay rate as a function of time for the bone sample of FIG. 2C;

FIG. 9A is a plot for the bone sample of FIG. 6A of time-dependent diffusion coefficients along two different directions measured with a compensated pulsed field gradient sequence, according to an embodiment of the invention;

FIG. 9B is a plot for the bone sample of FIG. 6B of time-dependent diffusion coefficients along two different directions measured with a compensated pulsed field gradient sequence, according to an embodiment of the invention;

FIG. 9C is a plot for the bone sample of FIG. 6C of time-dependent diffusion coefficients along two different directions measured with a compensated pulsed field gradient sequence, according to an embodiment of the invention;

FIG. 10A is a graph illustrating a comparison of DDIF data with bone surface-to-volume ratio derived from PFG time-dependent diffusion experiments;

FIG. 10B is a graph illustrating the fractional anisotropy of a surface-to-volume ratio tensor calculated from PFG time-dependent diffusion experiments;

DETAILED DESCRIPTION

There are two types of bone in the human body: cortical bone (a dense, compact bone existing in the middle of a long bone) and trabecular or cancellous bone (a more porous type of bone found generally near major joints and in the spine). Trabecular bone is comprised of a complex three-dimensional network of rods and plates. Most of the load-bearing capability of the skeleton is attributed to the trabecular bone region. The development or deterioration of trabecular bone structure is significantly affected by the mechanical forces it experiences.

Figure 1:
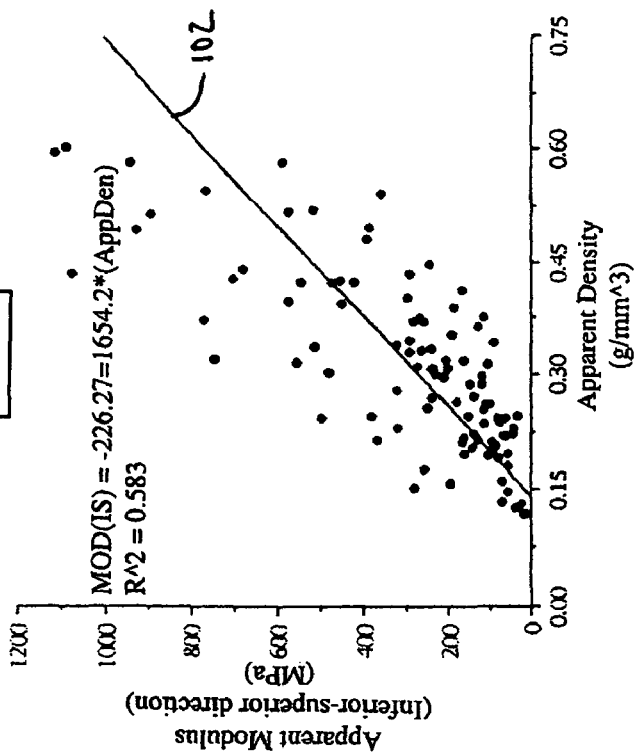
FIG. 1 is a graph illustrating a relationship between bone density and bone strength.

The mechanical strength of a bone specimen, and thus the risk of its fracturing, depends on several factors. One very important factor in bone strength is the amount of bone material, which is related to various parameters such as bone volume fraction (BVF), porosity, or the most common clinical parameter, bone mineral density (BMD). FIG. 1 illustrates a graph of a relationship between bone strength and BMD. Apparent modulus (in MPa), a measure of the bone strength, is represented on the vertical axis, and apparent density (BMD) is represented on the horizontal axis. Line 102 illustrates a correlation between the two quantities. As can be seen in FIG. 1, there is an extensive spread of bone strength at a given density. While a definite correlation between BMD and fracture occurrence exists, it is also clear that densitometry alone does not entirely predict the risk of fracture. This is because the details of the trabecular bone structure (e.g., the "bone quality") also contribute significantly to the bone strength and thus to the risk of fracture.

Trabecular bone includes combinations of rods and plates with thicknesses/diameters on the scale of 100 μm in an interconnected network. Bone structure changes are governed at the cellular level by osteocytes: osteoclasts, which control bone erosion, and osteoblasts, which control bone formation. If the overall bone remodeling performed by these two cell types is imbalanced, as is postulated to occur in osteoporosis, serious weakening can occur in the trabecular bone network. These changes have been extensively characterized within and between different human subjects as a function age using DXA, μCT or MRI, as is described in the literature. Structural indices such as mean trabecular thickness, mean trabecular separation and trabecular number can be calculated from microscopic images, and a wide variety of indices beyond these have been proposed to highlight structure, anisotropy, or correlation with strength. Many studies show that the parameter with the largest correlation with weakening is the trabecular number (also known as the trabecular plate density or surface density), which represents the number of trabeculae per unit length in a given direction. Trabecular widths are also known to decrease with age, but typically less dramatically than the trabecular number, and not sufficiently to explain the weakening in most cases.

This discrepancy is one of the motivations of a widely accepted model of bone degradation described in a paper by A. M. Parfitt (Bone 13, S41 (1992)) which is herein incorporated by reference in its entirety. This model rationalizes the fact that the only explanation for the observed progression in bone structure is not a uniform thinning of trabecular plates but a removal of entire plates with a consequent loss in connectivity. This removal is postulated to begin through a period of overactive osteoclastic resorption (bone removal) on a given trabecular plate that consumes the entire thickness at a certain point, opening a hole or "perforation" that connects previously isolated regions of marrow. These perforations grow until eventually all that remains of the original plate are rods that connect to other adjacent plates. The trabecular number parameter that tracks this process and that correlates well with strength is analogous to a projected surface-to-volume ratio (PSVR) along a given direction. As discussed further below, two NMR techniques employed in some embodiments of the invention may probe this projected surface-to-volume quantity.

Another important feature of trabecular bone is its anisotropy. Since many bones are under anisotropic mechanical load, their structure and development show anisotropy along the load direction. This anisotropy is often quantified with a "fabric tensor," describing both the amount of anisotropy and its orientation. The fabric tensor may be characterized through microscopic image measures such as mean intercept length (MIL), density autocorrelation lengths, or digital topology-based orientation analysis (DTA-O). Models have been developed that relate these tensor elements to mechanical elastic moduli, such as described, for example, in a paper by S. Cowin in Mechanics of Materials 4, 137 (1985)), which is herein incorporated by reference in its entirety. Furthermore, evidence exists that bone degradation can take place anisotropically, with transverse rod sections more likely to disappear than longitudinal ones in some cases or portions of the life cycle. According to some embodiments of the invention, there are described NMR techniques that may be suited to measure this anisotropy, as discussed below.

It is to be appreciated that this invention is not limited in its application to the details of construction and the arrangement of components set forth in the following description or illustrated in the drawings. The invention is capable of other embodiments and of being practiced or of being carried out in various ways, and the invention is not limited to the examples presented unless specifically recited in the claims. In addition, it is to be appreciated that the phraseology and terminology used herein is for the purpose of description and should not be regarded as limiting. The use of the words "including," "comprising," "having," "containing," or "involving," and variations thereof herein, is meant to encompass the items listed thereafter and equivalents thereof as well as additional items.

Referring to FIGS. 2A-2C, there are illustrated sections of processed three-dimensional μCT images of example cylindrical bovine bone samples that were used for measurements. Each figure shows, for a given sample, two slices (one perpendicular to the cylindrical axis, the other perpendicular to a radius) and a 3D reconstruction of a cubical section (2×2×2 mm) from the sample center. For clarity in the following discussion, the samples will be referred to as sample A (illustrated in FIG. 2A), sample B (illustrated in FIG. 2B) and sample C (illustrated in FIG. 2C). The approximate dimensions for each sample are 8 millimeters (mm) in height, 6 mm in width and 1 mm in thickness. In FIG. 2A, the image shows that the bone sample has a rarefied structure of loosely connected bone struts. FIG. 2B shows a higher concentration of highly connected struts, and FIG. 2C shows a set of quasi-parallel large plates. Qualitatively, this is a progression of low to high to low projected bone surface area along the load-bearing direction. The samples shown cover a range of mechanical yield stresses in a full sample set that was used for DDIF measurements in accordance with embodiments of the invention, from weak (2.4 MPa, FIG. 2A) to intermediate (6 MPa, FIG. 2B) to strong (34.5 MPa, FIG. 2C). Qualitative differences in density, shape and anisotropy of the trabecular elements may be observed in the images shown in FIGS. 2A-2C.

The inability to accurately predict fracture risk in osteoporosis patients presents a need for new technologies that can determine the microstructure of bones and correlate it to bone strength. Many different magnetic resonance techniques may be applied to the characterization of the structure of trabecular bone. As discussed above, nuclear magnetic resonance (NMR), magnetic resonance imaging (MRI) and microscopic computed tomography (μCT) techniques have all been used to obtain information about bone samples. These methods have seen significant development in the research community, but have yet to become the default clinical standard for various reasons. Thus, there is a need for a method that may efficiently (e.g., without requiring long scan times or high X-ray doses) provide useful information about bone quality.

To address this need, some aspects and embodiments of the present invention provided a method for trabecular bone strength determination using NMR and MRI techniques. In one embodiment, diffusion-based NMR and MRI methods may be used to characterize the structure of a bone sample, as discussed further below. Combining this measurement with the bone volume fraction (BVF) or BMD characterization and an empirically established correlation with mechanical properties of the bone, may provide an improved measure of bone strength using fully non-invasive techniques. Embodiments of methods for bone strength characterization described herein differ from conventional MRI techniques in that water diffusion may be used to characterize bone structure, and high resolution imaging may not required. As a result, the method may be suitable for clinical use and has potential for application as a routine MRI protocol.

Embodiments of the invention may provide two major advantages compared to the high resolution imaging approaches. One is that the invention may not require high resolution imaging which is difficult to perform clinically. Further, combining aspects of the DDIF method described herein with low-resolution imaging is clinically feasible. The second advantage may be that embodiments of methods according to the invention can provide a map of bone strength or a qualitative indicator thereof. Thus, it may provide bone strength evaluation over large area of bones and can be used to identify the weak portion within a bone.

According to one embodiment, a DDIF (decay due to diffusion in the internal field) based magnetic resonance method may be used to quantify the microstructure of trabecular bone for in vivo bone evaluation. A DDIF-based method can obtain pore sizes down to 1 μm, which is significantly better resolution than currently achievable by high-resolution MRI. Such high resolution may be achieved by monitoring water diffusion to obtain statistical properties of the internal structure of the bone. As discussed below, the DDIF data can be directly correlated with mechanical properties of the bone, and may provide a better indicator of bone strength than do conventional BMD. According to another embodiment, pulsed-field gradient (PFG) measurements may be performed to measure the surface-to-volume ratio of trabecular bones, a parameter that may also be directly correlated with bone strength, as well as with the DDIF data, as discussed below. In addition, PFG measurements may be used to probe bone anisotropy, another parameter that may correlate with bone strength. In general, PFG-NMR and DDIF provide similar information of bone structure since both measure diffusion properties and are sensitive to anisotropically restrictive boundaries. The alternative avenues of the internal field gradient and the applied field gradient each have different advantages, and their combined results may be complementary.

According to one embodiment, a nuclear magnetic resonance method may be used to obtain statistical properties of the trabecular structure, rather than high resolution imaging of the structure. This technique is referred to as decay due to diffusion in the internal field, or DDIF. In water-saturated rock, DDIF measurements have been shown to provide a pore size distribution. DDIF relies on the presence of a difference in magnetic susceptibility between the constituents of the materials of a sample. When the sample is subject to an external uniform magnetic field, $B^r$, the susceptibility contrast may induce magnetic field non-uniformity, called the internal field. This internal field may possess a "fingerprint" of the pore space, such as the length scale of the pores, because it is produced by the pore structure. The DDIF technique may monitor water diffusion through this non-uniform internal field and may determine pore structure from the diffusion dynamics, as discussed further below. DDIF techniques and applications have been reviewed in several publications including Concepts of magnetic resonance 18A, 97

(2003) and NMR Imaging in Chemical Engineering, edited by Stapf and Han, chapter 3.7, Wiley-VCH 2005.

As discussed above, trabecular bone is a highly porous material, comprising a network of trabeculae (bone rods and plates). The term "pore" as used herein in the context of trabecular bones refers to the spaces in between the trabeculae. For simplicity, trabecular bone can be considered to be a solid matrix with water filling the pore space. It is to be appreciated that this is an approximation, with the actual bone structure being more complex; however, the approximation is sufficient for the purposes of demonstration and explanation of embodiments of the invention. As such a structure, comprising two different constituents, trabecular bone has magnetic field inhomogeneity and thus the DDIF technique may be applied to trabecular bone. For the unique structure and the high porosity of trabecular bone (porosity ~80%), the internal field gradients mostly exist near the trabecular surfaces.

In general, the DDIF signal decay may depend on the specific features of the internal field distribution such as the spatial extent of the internal gradients. However, the probing length scale of the measurement is unambiguously given by the diffusion length of the spins according to equation (1) below for any pore geometry.

$$l = \sqrt{2D_0 \tau} \quad (1)$$

where l is the length scale, $D_0$ is diffusion constant and $\tau$ is the diffusion time. For the case of trabecular bones, the fast decay signals originate from the pore surface layer. Therefore, the DDIF result is closely related to the surface-to-volume ratio of the samples, as discussed further below.

Figure 3:
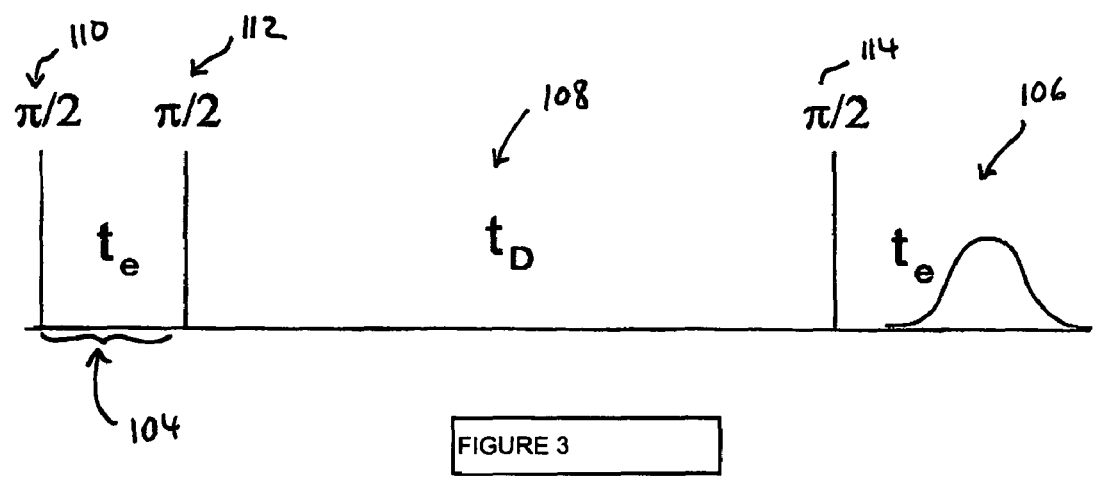
FIG. 3 is a pulse diagram illustrating one example of a DDIF simulated echo sequence according to an embodiment of the invention.

According to one embodiment, the DDIF technique may employ NMR pulse sequences in which the internal magnetic field of the sample material encodes structural information in the initial and final intervals of the sequence. One embodiment of a simulated echo pulse sequence is illustrated in FIG. 3 and may be described by:

$$\frac{\pi}{2} - t_e - \frac{\pi}{2} - t_D - \frac{\pi}{2} - t_e - \text{echo} \quad (2)$$

The notation π/2 denotes a radio frequency (RF) pulse that rotates the spin vector by 90 degrees, $t_e$ is the encoding time and $t_D$ is the diffusion time. IN at least one embodiment, the internal field may be present throughout the sequence and no external field gradient may be applied. Referring to FIG. 3, the first period 104 of the sequence may be a spatial encoding period (of duration $t_e$) and the third period 106 may be a spatial decoding period (also of duration $t_e$). The middle period 108 ($t_D$) is the diffusion period.

Qualitatively, the example may start by letting spins precess in the internal field for a time period of $t_e$. The first π/2 pulse 110 may rotate longitudinal magnetization into the transverse plane to precess at a frequency proportional to the local internal field $B^i$. During the encoding period 104, each spin acquires a phase that is proportional to its local magnetic field. As a result, the internal field variation within a pore may be encoded in the phase of the spins. More specifically, a precession phase difference may develop between spins at different positions, the precession phase modulation being given by:

$$\Phi = \gamma B^i t_e \quad (3)$$

where $\Phi$ is the phase modulation and $\gamma$ is gyromagnetic ratio of a proton. The phase modulation may follow the spatial characteristics of the internal field. For bone measurements, $t_e$ may be on the order of ten milliseconds. At the end of the encoding period 104, the spin magnetization is rotated to along the applied field direction to stop the precession. In one example, this rotation may be achieved using another π/2 pulse 112 that may tip the transverse magnetization back into the longitudinal direction. As a result, the spatial pattern of phase differences may be encoded as a spatial pattern of amplitudes of longitudinal magnetization.

After the encoding period, the spins may be allowed to diffuse for a time period of $t_D$. In one example of bone measurements, $t_D$ may range from one millisecond to several seconds. At the end of the diffusion period 108, the magnetization decay due to diffusion may be recorded by a third π/2 pulse 114 to provide the stimulated echo. If the diffusion distance during $t_D$ meets or exceeds the length scale of this modulation, the amplitude of the modulation will deteriorate and thus induce signal decay. The resulting signal attenuation as a function of the diffusion time, $t_D$, and may include a range of decay times determined by the distribution of internal field gradients in the specimen. In the case of trabecular bone, this distribution is in turn connected to the topology of the bone network.

In one embodiment, given the distributed response captured within a DDIF dataset, one method of data analysis is to use Laplace inversion. Laplace inversion refers to the decomposition of a signal into a sum of decaying exponential functions, and various conventional numerical techniques may be used to obtain a Laplace inversion spectrum from the DDIF dataset. After the inverse Laplace transform has been applied to the data, the resulting magnitudes $A_n$ for different decay times $\tau_n$ form a spectrum that is herein referred to as a DDIF spectrum.

Figure 4:
FIG. 4 is a pulse diagram illustrating one example of a DDIF reference sequence according to an embodiment of the invention.

During the diffusion time, another source of decay is due to spin-lattice relaxation, a process by which the spins lose memory of their excitation and return to equilibrium. According to one embodiment, a reference scan may be used to measure this dependence, which can also be distributed in general due to one or more of distribution of pore sizes, relaxivities, bulk relaxation. Referring to FIG. 4, there is illustrated one example of a reference scan that may be used to measure spin relaxation and provide reference data. The influence of this relaxation decay can then be separated from the DDIF data in the analysis stage.

A series of DDIF measurements were carried out on a range of bovine trabecular bone samples extracted from the tibiae. The data were acquired under the same conditions and with nominally equivalent pulse sequence parameters. These data were analyzed within the Laplace inversion formalism as described above. However, it is to be appreciated that the invention is not limited to the use of Laplace inversion to analyze the data and other techniques may also be used. For example, a similar analysis using an initial decay approach may produce qualitatively similar results. The DDIF data were compared for each bone sample to two other characterizations: a mechanical yield stress measurement and μCT imaging, as discussed further below.

DDIF examples were performed on the set of water-filled bone samples in a 2T (proton magnetic resonance frequency 85 MHz) horizontal widebore Nalorac magnet (Nalorac Cryogenics, Walnut Creek, Calif.) equipped with a Bruker Biospec spectrometer (Bruker Biospin, Billerica, Mass.). The orientation of the applied field was along the cylindrical axis of each sample, which was approximately the load-bearing axis of the parent tibiae from which each sample was extracted. DDIF and reference signals were collected for a range of logarithmically spaced diffusion times $t_D$ from 1 ms to 10 s, and a range of encoding times $t_e$ from 5 to 30 ms. It is to be appreciated, however, that the invention is not limited to the use of these example times, nor to the use of a logarithmically spaced series of diffusion times.

Referring to FIGS. 5A-5C, there are illustrated graphs of signal decay rates of the DDIF and reference scans applied to each of sample A, sample B, and sample C. FIG. 5A illustrates the signal decay graph corresponding to sample A, FIG. 5B illustrates the signal decay graph corresponding to sample B, and FIG. 5C illustrates the signal decay graph corresponding to sample C. In each of FIGS. 5A-5C, normalized signal decay is represented on the vertical axis and time (in seconds) is represented on the horizontal axis. The solid data points correspond to the DDIF scan for each sample and the open data points correspond to the reference scans for each sample. The data are arranged in order of increasing bone strength from FIG. 5A (corresponding to sample A shown in FIG. 2A) to FIG. 5C (corresponding to sample C shown in FIG. 2C). While the relaxation reference data is roughly equal for all samples, the DDIF data shows enhanced decay for sample B which has intermediate strength and high surface area (FIG. 5B).

Figure 6C:
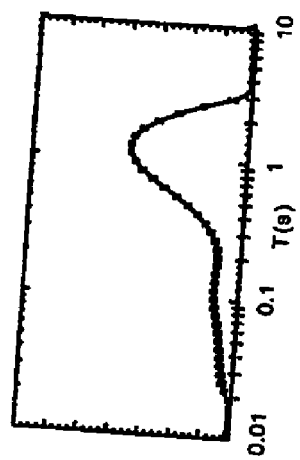
FIG. 6C is a plot of a DDIF spectrum for the bone sample of FIG. 6C.
Figure 6B:
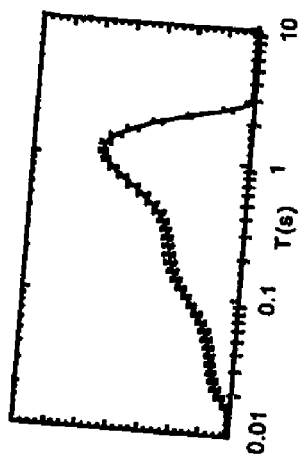
FIG. 6B is a plot of a DDIF spectrum for the bone sample of FIG. 6B.
Figure 6A:
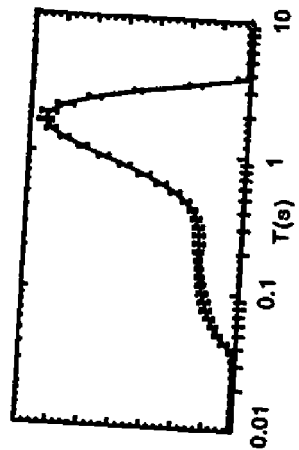
FIG. 6A is a plot of a DDIF spectrum for the bone sample of FIG. 6A.

As can be seen in FIG. 6, there is a correlation between signal decay rates and yield stress. Referring to FIG. 6A, there is illustrated the Laplace inversion spectrum for sample A. Similarly, the Laplace inversion spectra from samples B and C and shown in FIGS. 6B and 6C, respectively. An evolution of the weight in the fast diffusion mode portion of the spectrum (20 ms<T<600 ms) is evident, from low weight at weak strength, to a maximum weight near a yield stress of 6 MPa, and finally to low weight at high yield stress. The weight in the fast decay region grows continuously from 2.4 to 6 MPa, then falls to approximately the low strength value by the highest strength sample (34.5 MPa).

Figure 7:
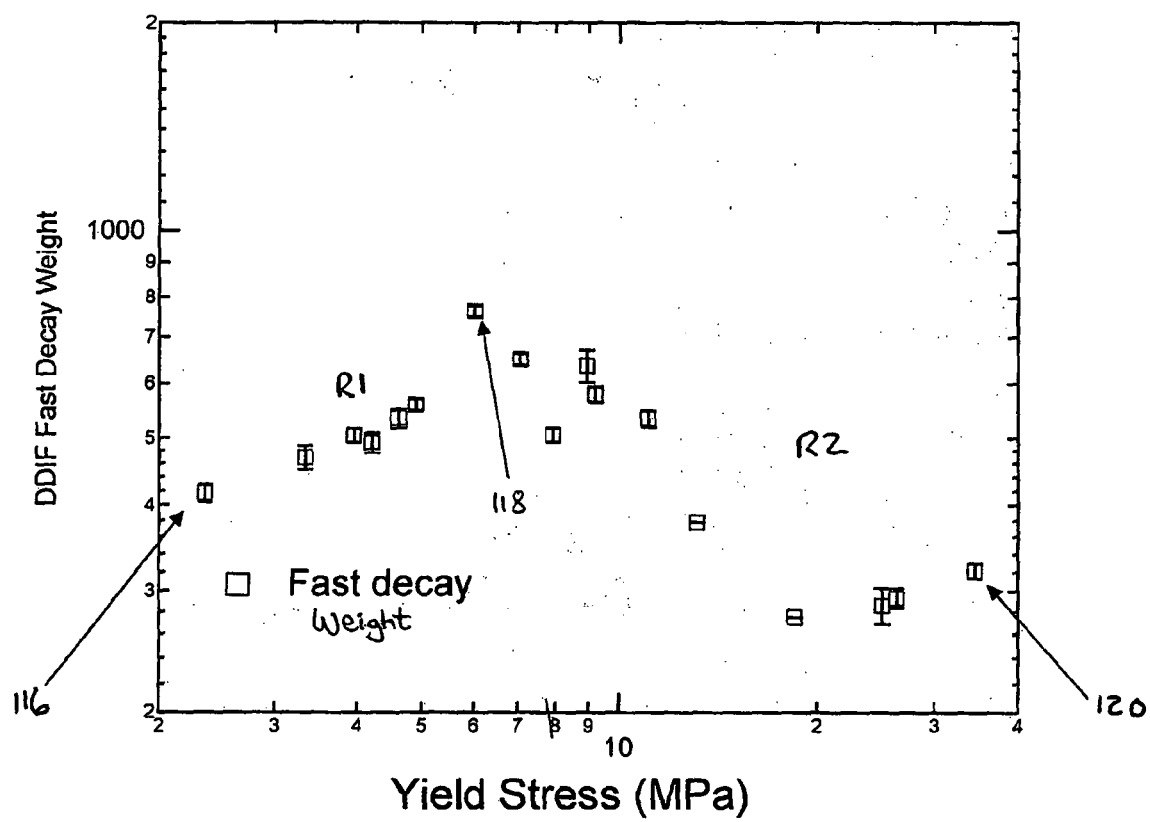
FIG. 7 is a graph of DDIF fast decay weight plotted against yield stress for a selection of bone samples.

This trend is quantitatively represented in FIG. 7 as an integral of the Laplace inversion spectrum over the relevant range as a function of yield stress. In other words, FIG. 7 illustrates the integrated decay weight in the fast decay region (20 ms<T<500 ms) plotted against yield stress (in MPa) on the horizontal axis. Error bars on the decay rate data points indicate variations in the results with different noise realizations. Data point 116 corresponds to sample A, data point 118 corresponds to sample B and data point 120 corresponds to sample C. The rise and fall of DDIF decay signal with bone strength is clear. There is an initial increase of the DDIF decay weight with increasing strength, to a maximum that occurs at a yield stress of approximately 6 MPa, followed by a decrease at higher strengths. Thus, the data may be divided into two regions, a "weak" region R1 and a "strong" region R2, on either side of the maximum 118. Interpretation of these results may be facilitated by comparison with data obtain from other NMR measurements and from image processing techniques, as discussed below.

According to another embodiment, time-dependent diffusion may be measured by pulse-field gradient NMR measurements. In one embodiment, another method that may be used to evaluate pore structure is to use pulsed field gradients (PFG) to directly measure the water diffusion coefficient. From the time dependent water diffusion coefficient, the surface-to-volume ratio of the medium can be determined, as discussed below. PFG-NMR and PFG-MRI applications are numerous in porous media research and biomedical imaging. However, the direct application of PFG-NMR to bone strength evaluation has been largely absent. In one embodiment, PFG diffusometry examples may be performed as a function of both diffusion time and diffusion-sensitizing gradient orientation. This information may allow unambiguous determination of bone surface-to-volume ratios as a function of orientation, thus probing the bone sample's topology and anisotropy.

Figure 8:
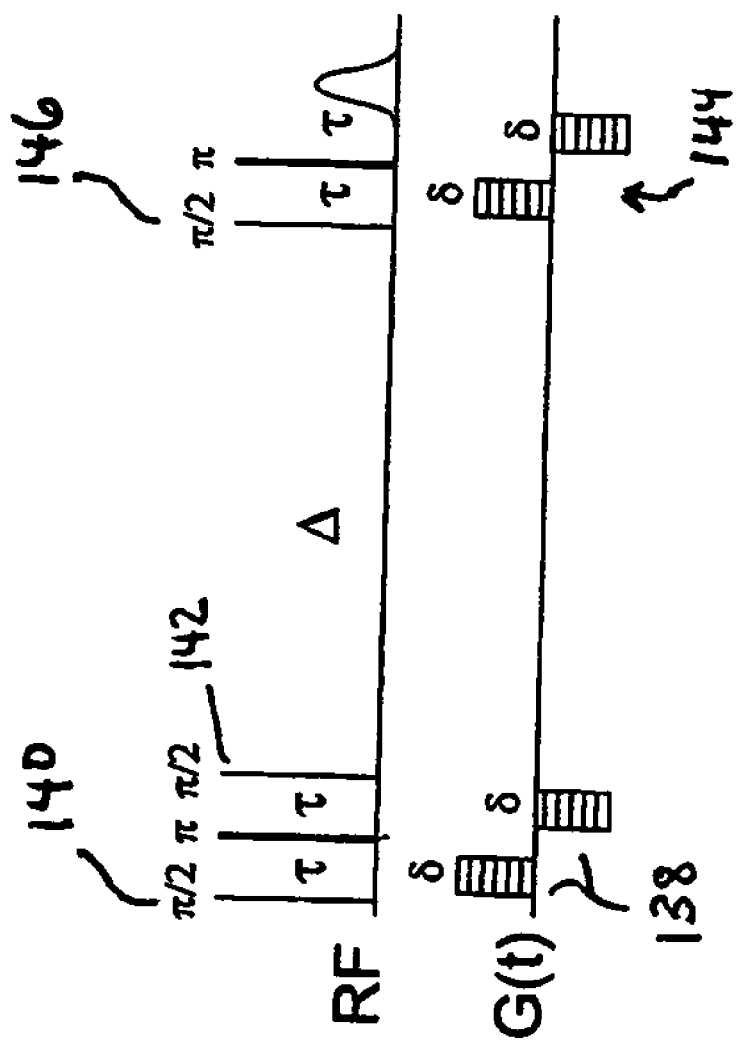
FIG. 8 is a pulse diagram of one example of a pulse sequence that may be used for pulse field gradient measurements according to an embodiment of the invention.

In one example, a PFG-NMR technique may employ a stimulated echo sequence with internal field compensation, an example of which is illustrated in FIG. 8. A bipolar gradient pulse 138 may be located between the first two π/2 RF (140) pulses and another bipolar gradient pulse 144 with identical width and amplitude may occur after the third π/2 RF pulse 146. Refocusing (π) pulses are also included to reverse the phase accumulation from internal field gradients. The diffusion decay at small gradients g follows an exponential form given by the equation:

$$\frac{S(g)}{S(0)} \approx \exp\left[-D(\Delta)(2\gamma g\delta)^2\left(\Delta + \frac{3}{2}\tau - \frac{\delta}{6}\right)\right] \quad (6)$$

where Δ is the diffusion time shown in FIG. 8 and δ is the duration of the gradient pulses. In porous media, the restriction of water diffusion gives rise to a time-dependence in the apparent diffusion coefficient (D) as the diffusion length approaches the pore length scale. In particular, the slope of the diffusion constant D as a function of Δ may determine the surface-to-volume ratio of the sample. In anisotropic media such as trabecular bone, this measurement may depend upon the relative orientation of the specimen and the applied field gradient. In PFG examples, the applied field gradient may be arbitrarily oriented. Therefore, a set of measurements with different orientations may be used to fully characterize the surface-to-volume ratio and its anisotropy.

In some examples, PFG measurements were conducted in the same magnet system with the same samples and sample holder as were the DDIF measurements described above. The z-axis gradient was oriented along the applied field and the samples' cylindrical axis. A stimulated echo sequence, such as that illustrated in FIG. 8, with internal field compensation was used to measure the apparent diffusion coefficient (ADC) along each gradient direction and for a series of different diffusion times Δ. A conventional stimulated echo sequence without internal field compensation can also be used to measure ADC. For a given diffusion time, a single ADC was determined by measuring the echo decay for fixed sequence timing and variable diffusion gradient strength g. For a set of samples, ADCs were measured along both the y and z directions for a range of diffusion times from Δ=200 ms to 3 s, with τ=2.5 ms and δ=2 ms. The bone diffusion datasets D(t) were normalized to that of bulk water value.

The behavior of the time-dependent diffusion coefficient in a restricted diffusion medium is well understood (for example, see P. N. Sen, Concepts of magnetic resonance 23A, 1 (2004)). The leading order behavior of D(t) is given by the equation:

$$\frac{D(t)}{D_0} \approx 1 - \frac{4}{3\sqrt{\pi}} \frac{S}{V} \sqrt{D_0 t} \quad (8)$$

when the diffusion time is short, $l_D=\sqrt{2D_0 t}\ll L_{pore}$. Here S/V is the surface-to-volume ratio (SVR) of the porous medium. This behavior holds regardless of the detailed microstructure of the restricting boundaries. It should be noted that this formula applies for one-dimensional diffusion and does not assume an isotropic value of SVR. This is the appropriate case for the highly anisotropic structure of trabecular bone. For the water-filled trabecular bone case, at the largest $t_D$ used of 3 s, the diffusion length is $l_D$~108 μm, which is significantly smaller than the average pore size of 1 mm shown in the μCT images. Thus, the full PFG dataset can be reasonably approximated by Equation (8), and a projected surface-to-volume ratio (PSVR) can be extracted for each sample.

Referring to FIGS. 9A-9C, there are illustrated the results of the time-dependent diffusion coefficient measurements along two different gradient directions for the three bone samples, sample A (results shown in FIG. 9A), sample B (results shown in FIG. 9B) and sample C (results shown in FIG. 9C). In each figure, FIG. 9A-9C, normalized D(t) is plotted against diffusion time Δ (in seconds) for a transverse gradient direction (y) and a longitudinal (or axial) gradient direction (z). Each sample shows a different amount of restriction and/or anisotropy. In FIG. 9A, the open data series 148 represents diffusion in the transverse y-direction and the closed data series 150 represents diffusion in the z-direction for sample A (see FIG. 2A). In FIG. 9B, the open data series 152 represents diffusion in the transverse y-direction and the closed data series 154 represents diffusion in the z-direction for sample B (see FIG. 2B). Similarly, in FIG. 9C, the open data series 156 represents diffusion in the transverse y-direction and the closed data series 158 represents diffusion in the z-direction for sample C (see FIG. 2C). The weakest sample, sample A, shows nearly unrestricted diffusion along both directions, consistent with its high porosity. The intermediate sample, sample B, shows restricted diffusion in both directions, with a more pronounced transverse than longitudinal restriction. Finally, the strongest sample, sample C, mainly shows restriction primarily transverse to the sample axis, giving it the maximum anisotropy of the three. This difference in anisotropic diffusion can be expected from the appearance of the samples as seen in the μCT images in FIGS. 2A-2C.

As described above, a projected surface-to-volume ratio can be extracted from each D(t) dataset for both the longitudinal and transverse directions. The surface-to-volume ratio dataset for the transverse (y) direction, referred to as $PSVR_y$ (data set 161), and the surface-to-volume ratio dataset for the z-direction, $PSVR_z$, (data set 160) are plotted along with the DDIF data (data set 162) as a function of mechanical yield stress in FIG. 10A. The error bars in the PSVR data in FIG. 10A are estimated from the variance of the measured D for bulk water sample. As can be seen in FIG. 10A, the correlation between the DDIF data 162 and the $PSVR_z$ data 160 is excellent in both the low and high strength regimes (regions R1 and R2, respectively). The $PSVR_y$ data shows a different trend that increases with strength in the R1 region and remains approximately constant in the R2 region.

As discussed above, the anisotropy of trabecular bone may be quantified with a fabric tensor, describing both the amount of anisotropy and its orientation. According to one embodiment, a measure of bone anisotropy may also be calculated from the PFG data which is related to the fabric tensor of the bone sample. Thus, the PFG measurements may provide a method for quantifying anisotropy without requiring high resolution imaging. In one example, no less than six measurements of PSVR along different directions are made and the SVR tensor can be fully determined including three eigenvalues and three directional parameters. This type of measurement is common within diffusion tensor imaging (DTI). Given the eigenvalues $\lambda_i$ of a rank 2 tensor (e.g. diffusion tensor or the fabric tensor), the fractional anisotropy (FA) is defined by the following equation:

$$FA = \sqrt{\frac{3}{2} \frac{\sum_i (\lambda_i - \langle\lambda\rangle)^2}{\sum_i \lambda_i^2}}, \ 0 < FA < 1 \qquad (9)$$

In one example, the FA may be obtained for the SVR tensor by measurements along z and y directions, with 2 assumptions: (1) alignment of the lab frame and principal frame, i.e. the measured values for PSVR are the eigenvalues of the SVR tensor, and (2) cylindrical symmetry, i.e. $PSVR_y = PSVR_x$. These assumptions are reasonable for this sample set and are supported by corresponding analysis of μCT images of the samples, as discussed further below. It is to be appreciated that the SVR tensor is not equivalent to the standard diffusion tensor, but instead reflects deviations of the water diffusion from the bulk value. The contrast amongst samples of different structure and strength may be maximized using this tensor.

Referring to FIG. 10B, there is illustrated a plot of the fractional anisotropy (FA) of the SVR tensor, calculated using Equation (9), as a function of yield stress. Again, two regimes of strength are evident: a weak regime (R1, with yield stress<7 MPa) with a roughly constant anisotropy, and a strong regime (R2, with yield stress>7 MPa) with an increasing anisotropy with yield stress. This is consistent with the images shown in FIGS. 2A-2C in which the stronger sample, sample C (FIG. 2C) can be seen to be more anisotropic than the weaker samples A and B (FIGS. 2A and 2B, respectively).

Figure 11A:
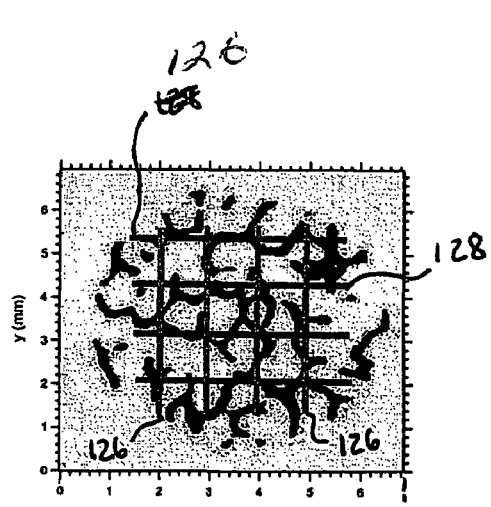
FIG. 11 is an illustration of a method for estimating mean intercept length in an image of a bone sample.
Figure 11B:
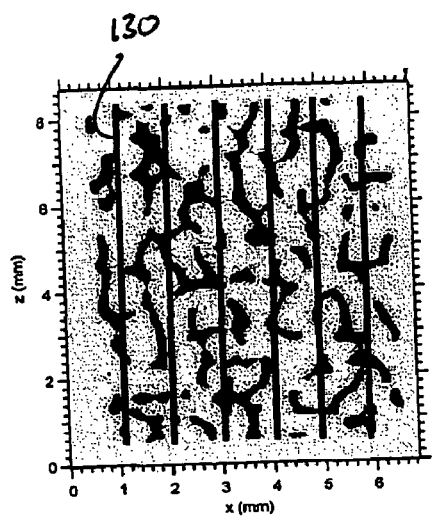

The anisotropy of the bone samples may also be described by another structural index, referred to as mean intercept length (MIL), which may be calculated from μCT images of the bone samples. To calculate the mean intercept length, a threshold technique may be used on the raw μCT images to divide the images into bone and water regions. Next, test lines may be drawn through the images of the sample along a given direction. For example, referring to FIG. 11A, there is illustrated an image of a sample with lines 126 drawn in the y-direction and lines 128 drawn in the x-direction. Similarly, in FIG. 11B, there is illustrated an image of the same sample with lines 130 drawn in the z-direction. The lengths of the free segments between regions of bone may then be counted along each line (in a given direction) and averaged over the whole sample. The result is referred to as the MIL for the given direction.

Figure 12:
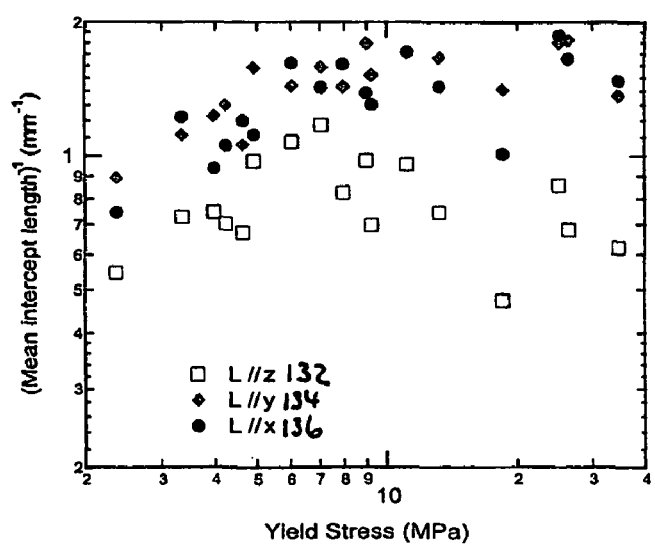
FIG. 12 is a plot of mean intercept length as a function of yield stress for a selection of bone samples.

Referring to FIG. 12, there is illustrated the MIL for the set of samples from which the above-described DDIF and PFG measurements were taken, displayed as inverse lengths for ease of comparison with other results. Yield stress in MPa is represented on the horizontal axis. Three sets of data points are plotted, series 132 measured in the z-direction, series 134 measured in the y-direction and series 136 measured in the x-direction. As can be seen with reference to FIG. 12, the inverse MIL values (series 134' and 136) for the two transverse directions (x and y) show a similar trend that increases in the weak bone regime and saturates to a constant in the strong regime, consistent with the trend in PSVRy (shown in FIG. 10A). The longitudinal inverse MIL (data series 132) is lower than the transverse values for all samples, and shows an increasing trend for the weak regime but a decreasing trend for the strong regime. The trend is similar to that measured with the NMR diffusion techniques (see, e.g. FIG. 10A), however with more scatter.

A vital characteristic of an indicator of fracture risk is its correlation with mechanical strength, represented in this case by the yield stress. Results from the two NMR techniques described herein, namely the DDIF measurements and PFG measurements, as well as reference to results of image analysis of the bone samples, reveal correlations with yield stress. Referring to Table 1, there are given the Pearson's correlation coefficients r obtained from linear fits showing the correlation of the measurements with yield stress and/or each other.

TABLE 1

|  | BVF | DDIF | $PSVR_z$ | $PSVR_y$ | $MIL_z$ | $MIL_y$ | $MIL_x$ |
|---|---|---|---|---|---|---|---|
| Yield Stress | 0.91 | 0.89 | 0.95 | 0.95 | 0.87 | 0.78 | 0.83 |
| BVF |  | 0.80 | 0.93 | 0.91 | 0.96 | 0.89 | 0.77 |
| DDIF |  |  | 0.84 | 0.80 | 0.67 | 0.65 | 0.88 |
| $PSVR_z$ |  |  |  | 0.99 | 0.76 | 0.80 | 0.79 |
| $PSVR_y$ |  |  |  |  | 0.82 | 0.72 | 0.73 |
| $MIL_z$ |  |  |  |  |  | 0.89 | 0.77 |
| $MIL_y$ |  |  |  |  |  |  | 0.72 |
| YS v. (A * BVF + B * index) |  | 0.94 | 0.97 | 0.94 | 0.96 | 0.92 | 0.93 |

Figure 13:
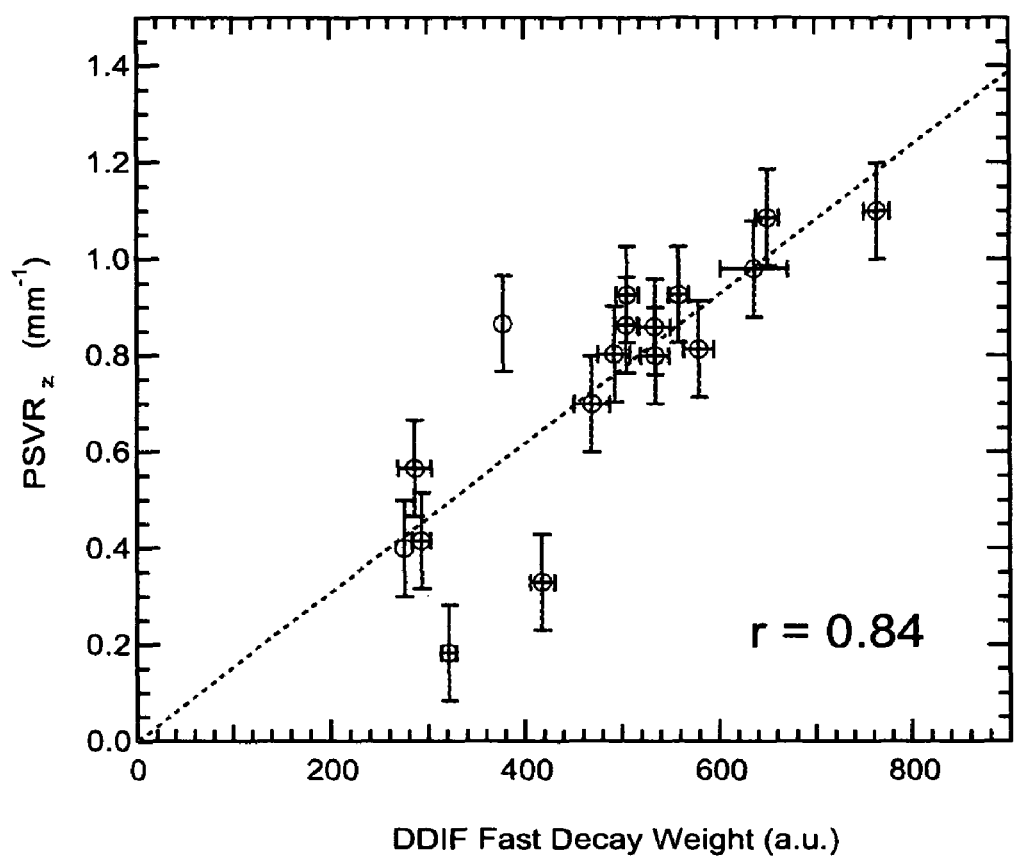
FIG. 13 is a graph illustrating a linear correlation between DDIF fast decay weight and projected surface to volume ratio $PSVR_z$.

Referring to FIG. 13, there is shown one example fit between the DDIF data and $PSVR_z$, which showed one of the highest correlations (r=0.84). This correlation, which is also found for a simpler initial decay analysis of the DDIF data, underlines the sensitivity of the DDIF scan to topological properties of the trabecular bone network. In fact, the progression with time of trabecular bone structure within the perforation model qualitatively parallels that shown by the sample set studied here. Strong, healthy bones comprised of parallel trabecular plates can deteriorate through bone resorption to network of interconnected rods/struts and finally to poorly connected rod groupings. Furthermore, it should be noted that given the anisotropy of trabecular bone structure and therefore the internal field distribution, the orientation of the applied field in the DDIF scan may be important, and its variation can provide more comprehensive structural details.

Since many of the compared indices show anisotropy, the complete sample set was included in the correlation only for analogous measurements (e.g. DDIF vs. $PSRV_z$ or $PVSR_y$ vs. $MIL_y$). For other cases, the yield stress correlation fits were performed in the weak strength regime of the sample set, from YS=2.4 MPa to 6.0 MPa, where the indicators all change monotonically with strength. The cases where the full sample set was used are shown in boldface.

The lowest row of Table 1 shows the correlation coefficient of a multilinear regression of yield stress versus a linear combination of bone volume fraction (BVF) and each of the other indices. This approach employs the new indices in a supplementary role to the bone volume fraction information. Note that the best benefit may be afforded with the inclusion of the $PSVR_z$ or $MIL_z$ data.

The dependence on strength shown in FIG. 10A for the two longitudinal NMR measurements performed on the bone sample set is noteworthy. It shows an initial increase with strength to an extremum that occurs at YS~7 MPa, and decreases for higher yield strengths. The same qualitative trend was obtained for the MIL indices derived from the μCT images (FIG. 12). Thus, the samples fall into two classes: a "weak" regime, corresponding to R1 on the figures, in which the bone samples are more isotropic, highly porous, and have relatively low strength, and a "strong" regime, corresponding to R2 in the figures, in which the samples are more anisotropic, less porous and have greater strength. The fact that the BVF-strength correlation was most improved with the inclusion of $PSVR_z$ data, which shows different behavior in the two regimes, supports this classification. These correlations indicate that the information regarding the bone structure and strength may be accessible in the DDIF measurement at an applied field (2 T) close to clinical values (1.5 or 3 T), and involves neither micro-imaging nor high applied gradients. This underscores its potential for application in clinical scanners.

A quantitative comparison of the results of these techniques is also worthwhile. All three longitudinal techniques (DDIF, $PSVR_z$, and $MIL_z$) show a dynamic range over the whole sample set of a factor of ~2. Those that are calibrated also display approximately the same absolute values (0.5<(S/V)<1.0 $mm^{-1}$). The transverse measurements, $PSVR_y$ and $MIL_{x,y}$, while showing equivalent qualitative trends, differ in the saturation value at high stress by a factor of 1.25. Reasonable quantitative agreement between the experimental NMR measurements and results from μCT image processing are found, which reinforces the NMR techniques' practical calibration.

While it is generally agreed that bone quality issues are vital to improved fracture risk assessment, the variety of scalar indices employed to characterize this quality is quite broad. The indices derived from micro-imaging techniques have a well-defined geometrical meaning, but those derived from bulk averaged measurements such as ($1/T_2'$) subscriplinewidth measurements, ultrasound, etc. are more empirical. For the diffusion-based NMR measurements (DDIF and D(t)), the quantitative diffusion length ($l_D=\sqrt{2D_0 t}$) lends a solid geometrical basis to the measurement.

In the D(t) case this translates to a quantitative measure of the surface-to-volume ratio along the gradient direction. As indicated by the close agreement between the two measurements, the DDIF signal is controlled by this parameter. This is a valuable connection, particularly since the inverse of the projected surface-to-volume ratio is closely related to the mean intercept length, which may be a dominant contribution in the trabecular number index.

The correlations of the structural indices described herein with strength, BVF, and each other are informative. To first order, good correlations (r>0.6) were obtained from all indices, measurement-derived or image-derived, both with strength and with each other. This result strengthens the interpretation that the diffusion NMR measurements may be controlled by the projected surface-to-volume ratio, similar to μCT image indices. Analyzing the list of correlations more carefully provides more insight on the relative advantages of the techniques. The best correlations with strength (in the weak regime of this sample set) are found with the NMR measurements (r~0.93) with slightly worse results from the image analysis techniques (r~0.80). Similarly, the best cross-correlations for the whole sample set are found between experimental NMR measurements (r~0.88), followed by image processing technique cross-correlations (r~0.77), with the lowest correlations when experimental NMR results are compared to image processing (r~0.74). Both NMR and image processing techniques correlate equivalently with BVF on average (r~0.88). One possible explanation for these correlation results is the difference in effective resolution. The minimum probing length of the NMR measurements, given by the smallest diffusion length probed, is on the order of a few μm, whereas the resolution of the μCT images is somewhat larger (34 μm). This may give the NMR based measurements access to a more accurate and complete projected surface-to-volume ratio than that derived from the CT images. However, it should be noted that another possibility is that the lower correlations from the CT image analysis arise from the limitations in the present computational algorithms.

Figure 15:
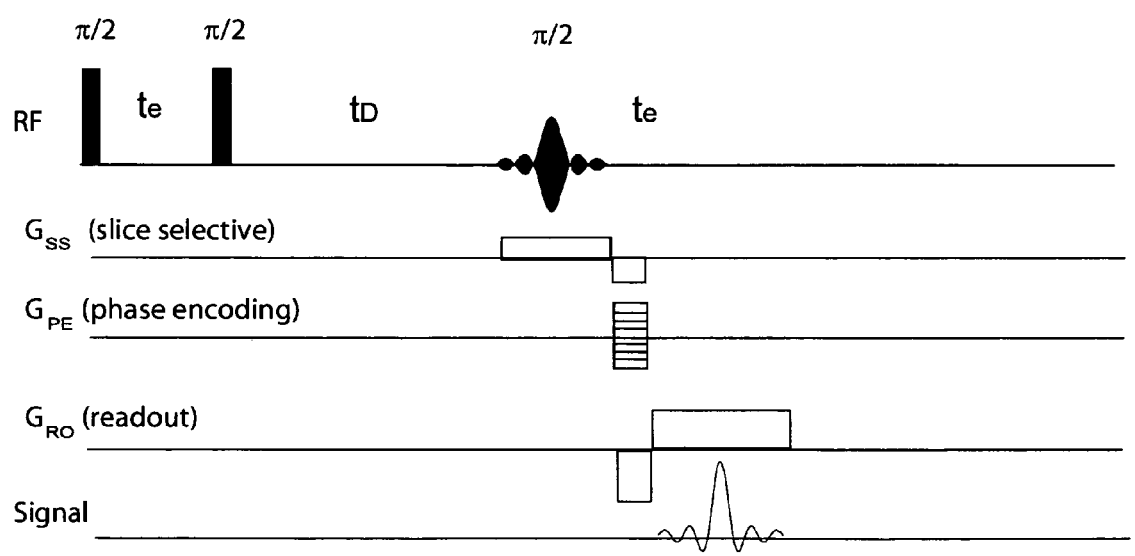
FIG. 15 is a pulse diagram of an MR imaging sequence for DDIF contrast containing a preparatory DDIF segment with a slice-selective final pulse and spin-warp imaging segment.

The non-monotonic behavior of the DDIF signal as a function of bone strength suggests that, currently, it alone may not provide an estimate of mechanical bone strength. However, when combined with the standard DXA bone density measurement, which is also individually insufficient for strength determination, a placement along the trend shown in FIG. 15 is possible. Given the aforementioned correlation of this trend with osteoporotic weakening, this placement has great clinical potential. The DDIF technique provides more topological information on the bone specimen than the more common bulk-averaged ($1/T_2'$) NMR parameter, but without the lengthy scan time and image processing required for high-resolution μCT or MRI. In this sense it could play a vital role as a compromise between information content and time in the arena of bone characterization.

The above sections demonstrate the principle and experimental tests of DDIF and PFG techniques for bone structure evaluation. The pulse sequences described in FIGS. 3, 4 and 8 can be directly used for in vitro samples of bones. However, for in vivo applications, spatial localization methods must be employed in order to isolate signals of bones from the surrounding tissues. Therefore, according to some aspects of the invention, there are provided methods to combine the diffusion-based techniques with in vivo MRI. There are described herein a few types of pulse sequences to combine DDIF and PFG with spatial localization using MRI techniques according to embodiments of the invention. It is to be appreciated that since the diffusion-based techniques provide information about the pore structure, the MRI resolution of the methods described here does not need to resolve individual trabeculae. For example, a voxel size of 1 mm or larger is most likely sufficient.

There can be two general approaches for including localization in DDIF and PFG. The first includes DDIF or PFG sequence as a weighting segment at the beginning of an imaging sequence, such as spin warp, EPI, RARE, FLASH, etc. A summary of these sequences can be found in a book by Callaghan (*Principles of Nuclear Magnetic Resonance Microscopy*. 1993, Oxford: Oxford University Press) which is hereby incorporated by reference. This approach is a natural extension of DDIF & PFG and is sometimes used in conventional diffusion-weighted imaging. The second approach uses 3D localization sequences in which the total signal originates exclusively from a prescribed voxel within the bone. Many 3D localization sequences can be used, such as STEAM, PRESS, and ISIS. For example, STEAM can provide DDIF contrast and spatial localization simultaneously. Here only a few examples will be discussed in detail to illustrate the concepts of the two approaches. However, it is to be appreciated that the invention is not limited to the specific examples described.

Figure 14:
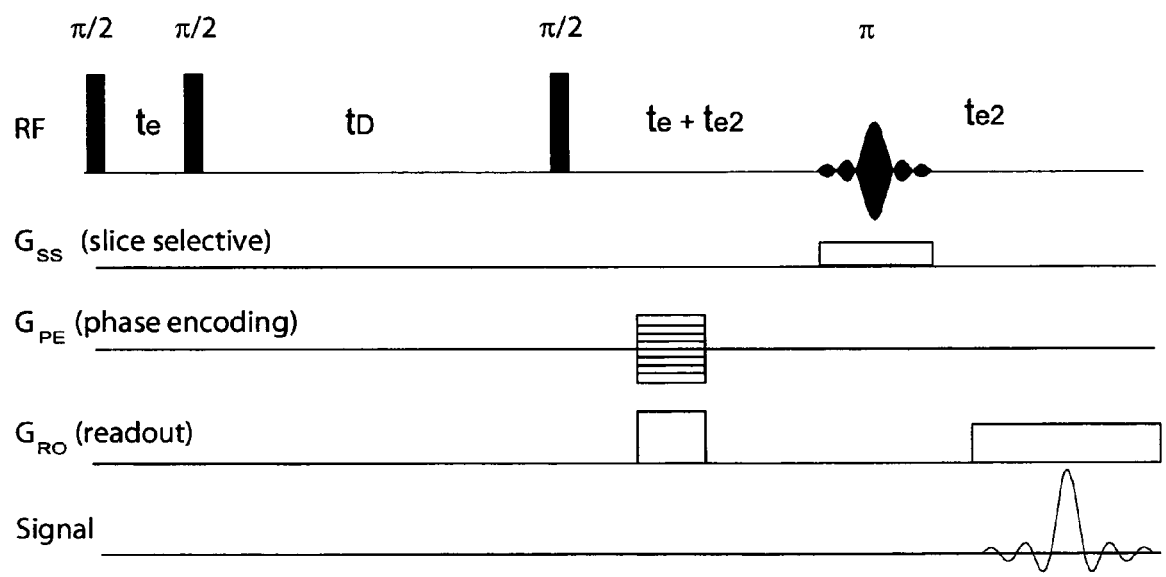
FIG. 14 is a pulse diagram of an MR imaging sequence for DDIF contrast containing a preparatory DDIF segment and a second-spin-echo spin warp imaging segment.

In one embodiment, DDIF (or PFG) may be used as a preparatory portion of the imaging sequence, shown in FIG. 14. Because DDIF may obtain structural information through diffusion, the imaging portion of the sequence may be of low resolution, thus reducing the scan time. In one embodiment, the sequence may comprise two parts, namely, the DDIF (or PFG) segment and the imaging segment. The DDIF segment may be the same as the standard DDIF sequence using three nonselective π/2 pulses and producing a stimulated echo at a time te after the last π/2 pulse. The imaging segment may include a slice-selective π pulse and the gradients (for slice selection, phase and frequency encodings) in a standard spin-warp combination. The π pulse may be at a time te+te2 after the third π/2 pulse and the final echo signal may be centered at a time te2 after the π pulse. The echo may be acquired for a series of phase encoding gradient steps to form a two-dimensional (2D) data set. Fourier transform of this data set will provide a 2D image of the bone, weighted by the DDIF segment. Then, 2D images with different $t_D$ may be acquired. From this data, DDIF spectra can be obtained for each pixel in a similar fashion as described earlier.

In another similar embodiment, the DDIF (or PFG) segment may remain almost as in FIG. 14, with one exception. Rather than performing the slice selection with a separate pulse, the third π/2 can be made slice selective, followed by a similar spin-warp methodology for image encoding of the stimulated echo, as illustrated in FIG. 15. This method may remove the need for another refocusing pulse and spin echo, along with its additional unwanted $T_2$ weighting. Such an approach incorporates the imaging gradients into the DDIF sequence without introducing diffusion weighting that might compete with the DDIF contrast. Note that overlapping echo pathways preferably may be eliminated through spoiling and/or phase cycling.

Figure 16:
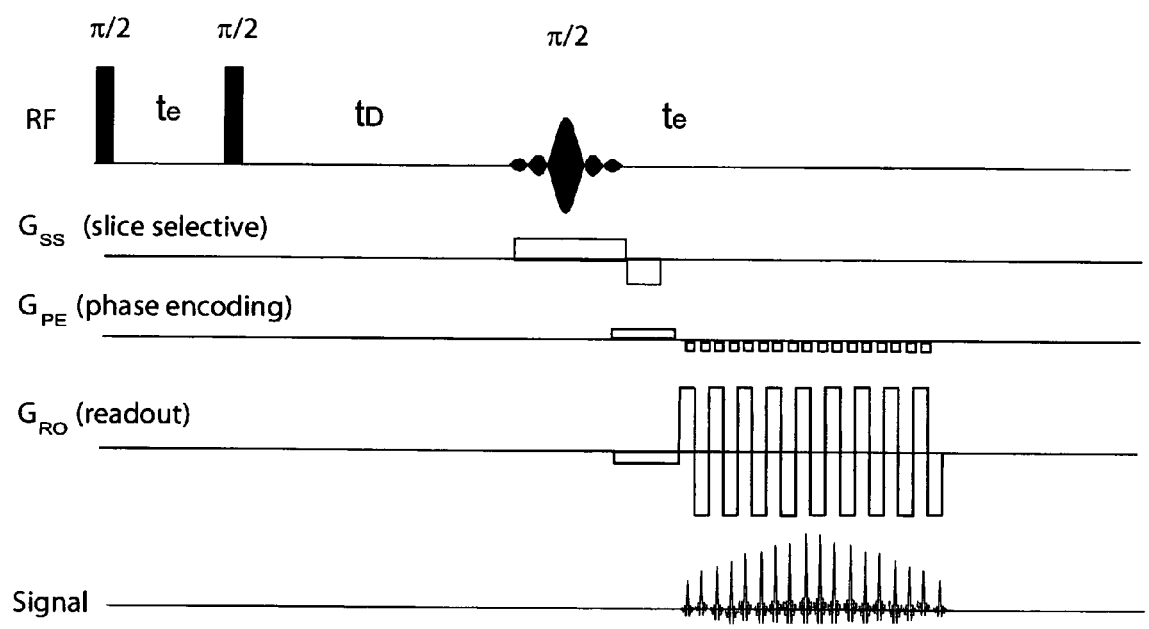
FIG. 16 is a pulse diagram of an MR imaging sequence for DDIF contrast containing a preparatory DDIF segment with a slice-selective final pulse and echo-planar imaging (EPI) segment.

In another embodiment, the DDIF (or PFG) segment may remain as illustrated in FIG. 15. The stimulated echo may be imaged with a single-shot imaging method called Echo Planar Imaging (EPI), which includes an alternating train of gradient pulses for both frequency and phase encoding, as illustrated in FIG. 16. In one embodiment, this EPI method may allow a set of gradient echoes to be acquired within a single scan that comprises the full 2D k-space dataset. Fourier transform of this data set will provide a 2D image of the bone weighted by the DDIF segment. In successive scans, 2D images with different $t_D$ can be acquired. DDIF spectra may be obtained for each pixel in a similar fashion as described earlier.

Figure 17:
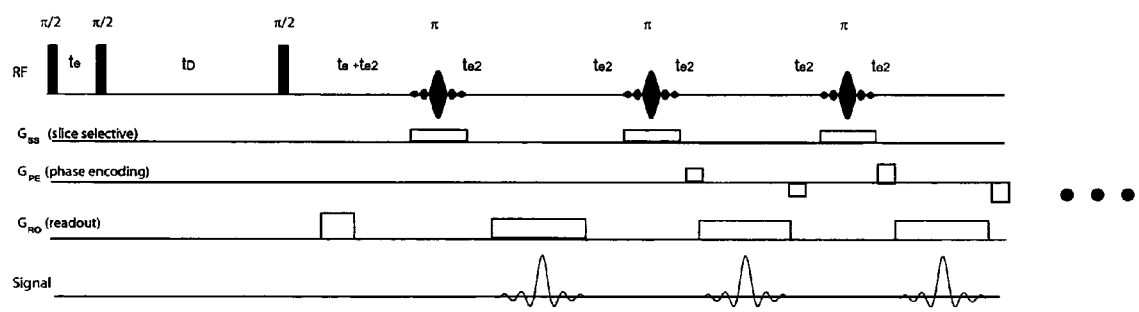
FIG. 17 is a pulse diagram of an MR imaging sequence for DDIF contrast containing a preparatory DDIF segment and a fast-spin-echo (FSE) imaging segment.

In another embodiment, the DDIF (or PFG) segment may remain as in FIG. 14. The imaging segment may include a slice-selective π pulse at a time te+te2 after the third π/2 pulse which may generate an echo centered at a time te2 after the π pulse. This echo can be further refocused by a train of π pulses that are 2*te2 apart producing a train of echoes. These echoes can be phase and frequency encoded to produce the 2D data set. This technique is called Fast Spin Echo Imaging (as well as Turbo Spin Echo or Rapid Acquisition w/Relaxation Enhancement (RARE)) and can allow a two-dimensional data to be acquired in much shorter time than the spin-warp method, while introducing some relaxation ($T_2$) contrast and/or image blurring as is illustrated in FIG. 17. Fourier transform of this data set will provide a 2D image of the bone weighted by the DDIF segment. Then, 2D images with different $t_D$ may be acquired. DDIF spectra will be obtained for each pixel in a similar fashion as described earlier.

In another embodiment, the DDIF (or PFG) segment may remain as in FIG. 14. The imaging segment may include a 3D localization sequence to select one volume voxel, instead of capturing a full image. Such 3D localization sequences include stimulated echo acquisition mode (STEAM), point resolved spectroscopy (PRESS) and image selected in vivo spectroscopy (ISIS) sequences. A summary of these sequences can be found in a text by Callaghan, P. T. in *Principles of Nuclear Magnetic Resonance Microscopy*. 1993, Oxford: Oxford University Press herein incorporated by reference in its entirety. The signal from these sequences may be derived exclusively from a voxel within the bone at an arbitrary location determined by the appropriate use of RF pulses and gradients. The signal may also be pre-weighted by the DDIF segment. In multiple scans, signals with different $t_D$ can be acquired. DDIF spectra may be obtained for this voxel in a similar fashion as described earlier.

Figure 18:
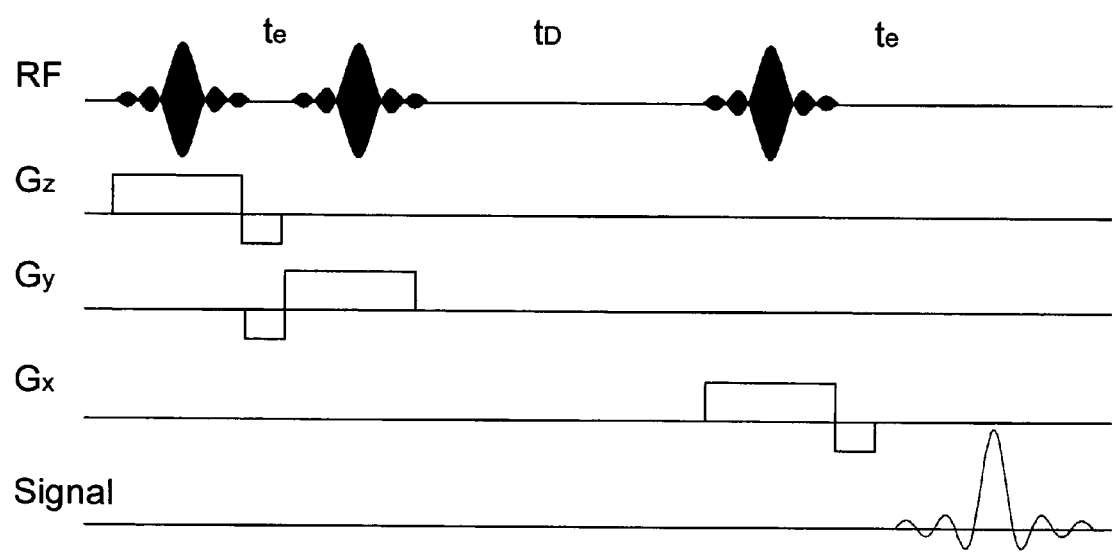
FIG. 18 is a pulse diagram of an MR imaging sequence for DDIF contrast containing a 3D localization STEAM imaging segment.

In another embodiment, the 3D localization and the DDIF (or PFG) contrast can be achieved simultaneously. One example of the 3D localization sequences as illustrated in FIG. 18. This sequence may include three slice selective π/2 pulses along three orthogonal directions which can be applied at time intervals required by the DDIF contrast. In multiple scans, the diffusion time $t_D$ can be varied, and a set of signals for the selected voxel can be obtained. DDIF spectra may be obtained for this voxel in a similar fashion as described earlier.

According to aspects and embodiments of the invention, NMR probes of trabecular bone structure have been demonstrated on a set of bovine trabecular bone samples and compared with several established characterizations. The NMR methods both employ the measurement of magnetization decay due to diffusion in magnetic field gradients. In one embodiment (DDIF) these gradients are in the variation of the internal field due to the susceptibility variation between bone and water (or soft tissue). In another embodiment, (D(t) or PFG), the gradients are externally applied in a sequence that compensates for the diffusion weighting of the internal gradients. Both examples demonstrate a non-monotonic dependence on the mechanical yield stress of the sample set, a trend that is determined by the projected surface-to-volume ratio along the load-bearing axis of the trabecular bones. This trend was also found by two methods of analysis of microimages of the same samples obtained by microscopic μCT imaging. These correlations show that the diffusion NMR methods may provide a reliable indication of bone strength and may thus be used to assess bones, without the need for high resolution imaging since they provide measures that are equivalent to some of those obtained through imaging. Thus, the NMR methods may provide a useful intermediate between two measurement extremes: the NMR linewidth ($T_2'$) (a simple, bulk averaged index) and a microscopic image (which requires long scan time). This intermediate has potential to play an important clinical role in improving fracture prediction, risk assessment, and screening for osteoporotic patients.

Having thus described several aspects and embodiments of the invention, modifications and/or improvements may be apparent to those skilled in the art and are intended to be part of this disclosure. It is to be appreciated that the invention is not limited to the specific examples described herein and that the principles of the invention may be used in a wide variety of applications. The above description is therefore by way of example only, and includes any modifications and improvements that may be apparent to one of skill in the art. The scope of the invention should be determined from proper construction of the appended claims and their equivalents.

What is claimed is:

1. A method of strength estimation for a trabecular bone by identifying structural parameters and properties of the trabecular bone, the method comprising:
   a) using a magnetic resonance technique that provides signals for measuring molecular diffusion over two or more diffusion time periods of different duration by monitoring characteristics of a net molecular displacement inside the trabecular bone so as to provide measured data;
   b) measuring the molecular diffusion at the two or more diffusion time periods and storing the measured data in a processor;
   c) using the stored data to derive at least one parameter that is related to a structure of the trabecular bone; and
   d) estimating the strength of the trabecular bone from the derived at least one parameter by comparing the derived at least one parameter with data relating to known properties of trabecular bones.

2. The method according to claim 1, further comprising calculating a bone volume fraction of the trabecular bone and wherein estimating the strength of the trabecular bone includes estimating the strength of the trabecular bone based on one of the at least one parameter and the calculated bone volume fraction, other prerecorded data or some combination thereof.

3. The method according to claim 1, further comprising calculating a bone mineral density of the trabecular bone wherein estimating the strength of the trabecular bone includes estimating the strength of the trabecular bone based on one of the at least one parameter and the calculated bone mineral density, other prerecorded data or some combination thereof.

4. The method according to claim 1, wherein deriving the at least one parameter includes deriving a surface-to-volume ratio of the trabecular bone.

5. The method according to claim 1, wherein measuring includes performing a decay from diffusion in an internal field (DDIF) measurement on the trabecular bone to obtain measured DDIF decay data.

6. The method according to claim 5, further comprising performing a Laplace inversion on the measured DDIF decay data to provide a DDIF spectrum.

7. The method according to claim 1, wherein measuring includes performing a pulsed-field gradient measurement on the trabecular bone to obtain measured apparent diffusion coefficient (ADC) data.

8. The method according to claim 7, further comprising performing a fit on the measured ADC data to obtain the projected surface to volume ratio.

9. The method according to claim 1, wherein measuring includes performing a pulsed-field gradient measurement on the trabecular bone using field gradients along different directions.

10. The method according to claim 9, further comprising performing a fit on the measured ADC data to obtain the surface to volume tensor.

11. The method according to claim 1, wherein the data is from the group consisting of one of trend data determined from repeating steps (a) to (d) and data relating known properties of one or more other similar trabecular bones or trend data determined from repeating steps (a) to (d) and data relating to determined properties of the trabecular bone.

12. The method according to claim 1, wherein the monitored characteristics of the net molecular displacement is measuring the change of spin magnetization due to molecular diffusion over diffusion time.

13. A method of characterizing a structural property for a body part by identifying structural parameters and properties of the body part, the method comprising:
   a) using a magnetic resonance technique that provides signals for measuring molecular diffusion over two or more diffusion time periods of different duration by monitoring characteristics of a net molecular displacement inside the body part so as to provide measured data;
   b) measuring the molecular diffusion at the two or more diffusion time periods and storing the measured data in a processor;
   c) using the stored data to derive at least one parameter that is related to a structure of the body part; and
   d) characterizing the structural property of the body part from the derived at least one parameter by comparing the derived at least one parameter with data relating to known structural properties of other similar body parts.

14. The method according to claim 13, wherein the body part is one of a bone or a trabecular bone.

15. The method according to claim 13, wherein the data comprises previously recorded data from at least one similar body part.

16. The method according to claim 13, wherein the at least one parameter is from the group consisting of one of a calculated body part density, an estimated body part strength, an estimated body part strength based on the derived at least one parameter and the calculated body part density, a body part surface-to-volume ratio, a quantitative measure of the surface-to-volume ratio along a gradient direction, a body part porosity, an amount of the body part material, an orientationally weighted surface to volume ratio or one or more pore size of the body part.

17. The method according to claim 13, wherein the body part structural property is from the group consisting of one of a measure of water diffusion, at least one mechanical property, one or more structural indices, a fracture risk assessment, a structural risk assessment or an anisotropy.

18. The method according to claim 17, wherein the measure of water diffusion is measured over a periodic period to obtain statistical properties of an internal structure of the body part.

19. The method according to claim 18, wherein the periodic measurements of water diffusion over time provides a pore size distribution of the body part.

20. The method according to claim 17, wherein the body part is a trabecular bone and the one or more structural indices are calculated, such that the one or more structural indices include one of a mean trabecular thickness, a mean trabecular separation, trabecular number or any combination thereof.

21. The method according to claim 17, wherein the at least one mechanical property includes one of a strength, a yield stress or a relation between a stress and a strain.

22. The method according to claim 17, wherein the anisotropy includes a structural index, such as a mean intercept length (MIL), that is calculated from μCT images of the body part.

23. The method according to claim 17, wherein the anisotropy includes a fabric tensor describing an amount of anisotropy and an orientation, such that the fabric tensor is characterized through a microscopic image which measures one of a mean intercept length (MIL), a plurality of density autocorrelation lengths or a digital topology-based orientation analysis (DTA-O).

24. The method according to claim 13, wherein measuring includes performing a decay from diffusion in an internal field (DDIF) measurement on the body part so as to obtain measured DDIF decay data, such that the body part is a trabecular bone.

25. The method according to claim 24, further comprising performing a Laplace inversion on the measured DDIF decay data to provide a DDIF spectrum.

26. The method according to claim 13, wherein measuring includes performing a pulsed-field gradient measurement on the body part to obtain measured apparent diffusion coefficient data, such that the body part is a trabecular bone.

27. A method of estimating a mechanical property for a trabecular bone by identifying structural parameters and properties of the trabecular bone, the method comprising:
   a) using a magnetic resonance technique that provides signals for measuring molecular diffusion over two or more diffusion time periods of different duration by monitoring characteristics of a net molecular displacement inside the trabecular bone so as to provide measured data;
   b) measuring the molecular diffusion at the two or more diffusion time periods and storing the measured data in a processor;
   c) using the stored data to derive at least one parameter, wherein the at least one parameter relates to the mechanical property of the trabecular bone, such that the mechanical property includes one of a strength, a yield stress or a relation between a stress and a strain; and
   d) estimating the mechanical property of the trabecular bone from the derived at least one parameter by comparing the derived at least parameter with data relating to known mechanical properties of other similar trabecular bones.

28. The method according to claim 27, wherein the at least one parameter is from the group consisting of one of a calculated trabecular bone density, a trabecular bone surface-to-volume ratio, a quantitative measure of the surface-to-volume ratio along a gradient direction, a trabecular bone porosity, an amount of the trabecular bone material, an orientationally weighted surface to volume ratio or one or more pore size of a portion of the trabecular bone.

* * * * *